United States Patent
Horn et al.

(10) Patent No.: US 7,408,023 B2
(45) Date of Patent: Aug. 5, 2008

(54) PEPTOIDS INCORPORATING CHEMOSELECTIVE FUNCTIONALITIES

(75) Inventors: Thomas Horn, Berkeley, CA (US); Ronald N. Zuckermann, El Cerrito, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 0 days.

(21) Appl. No.: 11/398,576

(22) Filed: Apr. 4, 2006

(65) Prior Publication Data

US 2006/0188916 A1    Aug. 24, 2006

Related U.S. Application Data

(62) Division of application No. 10/117,841, filed on Apr. 5, 2002, now Pat. No. 7,030,216.

(60) Provisional application No. 60/282,115, filed on Apr. 6, 2001.

(51) Int. Cl.
*C07K 2/00* (2006.01)

(52) U.S. Cl. .................. 530/300; 530/333; 530/334; 530/345; 514/2; 435/91.1

(58) Field of Classification Search ............ 514/2; 530/300, 333, 334, 345; 435/91.1
See application file for complete search history.

(56) References Cited

U.S. PATENT DOCUMENTS

| 4,406,826 | A |   | 9/1983  | Morgan et al.           |
|-----------|---|---|---------|-------------------------|
| 5,066,716 | A |   | 11/1991 | Robey et al.            |
| 5,286,846 | A |   | 2/1994  | Inman et al.            |
| 5,391,711 | A | * | 2/1995  | Funakoshi et al. 530/344 |
| 5,719,256 | A |   | 2/1998  | Tamai et al.            |
| 5,831,005 | A |   | 11/1998 | Zuckermann et al.       |
| 5,877,278 | A |   | 3/1999  | Zuckermann et al.       |
| 5,977,301 | A |   | 11/1999 | Zuckermann et al.       |
| 6,476,190 | B1|   | 11/2002 | Kent et al.             |
| 6,492,460 | B2| * | 12/2002 | Haq et al. 525/50       |

\* cited by examiner

*Primary Examiner*—David Lukton
(74) *Attorney, Agent, or Firm*—Mark Seka; Emily M. Haliday

(57) ABSTRACT

Molecules having potential biological activity, particularly peptoids, that are conjugated to solid phase supports, spacer groups, and/or ligation moieties, and methods of their preparation, are described. In some instances, the molecules of the invention are made entirely by solid phase synthesis. In other instances, the spacer groups are hydrophilic and compositions containing them, and to solid phase synthesis of varied structure peptoids using chemoselective ligation moieties.

10 Claims, 15 Drawing Sheets

PEPTOIDS INCORPORATING CHEMOSELECTIVE FUNCTIONALITIES

CROSS REFERENCE TO RELATED APPLICATIONS

This application is a divisional application of U.S. application Ser. No. 10/117,841, filed Apr. 5, 2002, now U.S. Pat. No. 7,030,216 which claims the benefit of U.S. Provisional Application No. 60/282,115, filed Apr. 6, 2001, which are hereby incorporated herein in their entirety.

FIELD OF THE INVENTION

The present invention relates to conjugates of molecules having potential biological activity, particularly peptoids, with solid phase supports, spacer groups, and/or ligation moieties, and methods of their preparation entirely by solid phase synthesis. The invention also relates to hydrophilic spacer groups and compositions containing them, and to solid phase synthesis of varied structure peptoids via the use of chemoselective ligation moieties.

BACKGROUND OF THE INVENTION

Solid phase stepwise synthesis has become a ubiquitous technique for the preparation of various oligomeric or polymeric molecules, such as oligonucleotides and oligonucleotide analogs, peptides, peptoids, and oligosaccharides. Frequently, the molecules are biologically active or are candidates for a biological activity. The technique is valued for its high efficiency, allows preparation of diverse arrays or libraries of molecules, which may remain bound to the solid support, and is readily amenable to automation.

In many cases, it is desirable to conjugate the molecules to other molecular moieties, such as other biomolecules (e.g. peptoids linked to oligonucleotides), masked linking groups, or spacer groups. Such conjugation may require solution phase reaction or time consuming modifications to otherwise automated syntheses. Therefore, it would be useful to provide methods of such conjugation that can be carried out entirely in the solid phase, with minimal disruption to automated synthetic protocols.

SUMMARY OF THE INVENTION

The present invention includes, in one aspect, a method of attaching a spacer group to a molecule preferably selected from a peptoid, a peptide, an oligonucleotide, and an oligosaccharide. The method comprises: synthesizing the spacer group, via initial reaction with an amine, hydroxyl or thiol group of the molecule, by repeating alternating addition of (i) a submonomer consisting of acrylic acid, an alkanoic acid bearing a terminal leaving group, or an activated derivative thereof, and (ii) a submonomer consisting of an alkanethiol having a terminal primary amine, hydroxyl or thiol group. In selected embodiments, submonomer (i) is acrylic acid or an activated derivative thereof, and submonomer (ii) is an alkanethiol having a terminal primary amine, for example, 2-aminoethanethiol, 2-hydroxyethanethiol, or 1,2-ethanedithiol. The method may further comprise converting sulfide linkages in the spacer group to sulfoxide linkages.

In one embodiment, the molecule bears an amine group, and the initial reaction is with the amine group of the molecule, thereby forming an amide linkage. The molecule may be attached to a solid phase support, and may itself be synthesized on the solid phase support. For example, when the molecule is a peptoid, the peptoid can be synthesized on an amine- or hydroxyl-derivatized solid support, by repeating alternating addition of (i) an acyl submonomer bearing an α-leaving group and (ii) a primary amine submonomer.

The method may further comprise attaching a ligation moiety to a free terminus of the spacer group.

In one embodiment, the amine of the amine-derivatized support is attached to a ligation moiety, and the amine is cleavable from the support. Such ligation moieties may comprise a functional group selected from the group consisting of: thiol, carboxylic acid, thioester, thiocarboxylic acid, aldehyde, hydrazine, hydrazide, 3-mercapto-1,2-propanediyl, aminooxyacetamide, N-(2-thioethyl)aminoacetamide, N-(2-hydroxyethyl)aminoacetamide, 2-bromo amino acid, biotin, and protected derivatives thereof.

In a related aspect, the invention provides a method of attaching a spacer group to a molecule preferably selected from a peptoid, a peptide, an oligonucleotide, and an oligosaccharide, having a acrylamide group at a terminus. This method comprises: synthesizing the spacer group, via initial reaction with the acrylamide, by repeating the steps of (i) reacting the thiol functionality of a hydroxyalkanethiol with the terminus of the molecule; and (ii) converting the hydroxyl functionality of the reacted hydroxyalkanethiol to a leaving group. This method may further comprise converting sulfide linkages in the spacer group to sulfoxide linkages.

In another aspect, the invention provides a method of preparing a spacer-molecule conjugate on a solid support, where the molecule is preferably selected from a peptoid, a peptide, an oligonucleotide, and an oligosaccharide. The method comprises: (a) synthesizing a spacer group on an amine- or hydroxyl-derivatized solid support, by repeating alternating addition of (i) a submonomer consisting of acrylic acid, an alkanoic acid bearing a terminal leaving group, or an activated derivative thereof, and (ii) a submonomer consisting of an alkanethiol having a terminal primary amine, hydroxyl or thiol group; and (b) attaching the molecule to the spacer. Such attaching may comprise synthesizing a peptoid, attached to an amino, hydroxyl or thiol group of the spacer, by repeating alternating addition of (i) an acyl submonomer bearing an α-leaving group and (ii) a primary amine submonomer.

In selected embodiments of this method, the solid support is amine-derivatized. In one such embodiment, the amine of the amine-derivatized support is attached to a ligation moiety, and the amine is cleavable from the support. The method may further comprise attaching a ligation moiety to the molecule, and/or converting sulfide linkages in the spacer group to sulfoxide linkages.

In one embodiment, the solid support is a planar array comprising a plurality of spacer groups, and the peptoid synthesizing comprises synthesizing a plurality of different-sequence peptoids, such as a combinatorial library of peptoids, attached to the spacer groups. In another embodiment, the solid support is a plurality of beads, and the peptoid synthesizing comprises synthesizing a plurality of different-sequence peptoids, such as a combinatorial library of peptoids, attached to the beads, wherein each bead contains same-sequence peptoids.

The invention also provides another method of preparing a spacer-molecule conjugate on a solid support, where the molecule is preferably selected from a peptoid, a peptide, an oligonucleotide, and an oligosaccharide. This method comprises: (a) synthesizing a spacer group on an acrylamide-derivatized solid support, by (i) reacting the thiol functionality of a hydroxyalkanethiol with the acrylamide; and repeating the steps of: (ii) converting the hydroxyl functionality of the reacted hydroxyalkanethiol to a leaving group, and (iii) reacting the thiol functionality of a hydroxyalkanethiol with the leaving group; followed by (b) attaching the molecule to the spacer. This method may further comprise converting sulfide linkages in the spacer group to sulfoxide linkages.

In another aspect, the invention provides a method of preparing a solid support derivatized with hydrophilic spacer groups. This method comprises: (a) synthesizing spacer groups on an amine- or hydroxyl-derivatized solid support, by repeating alternating addition of (i) a submonomer consisting of acrylic acid, an alkanoic acid bearing a terminal leaving group, or an activated derivative thereof, and (ii) a submonomer consisting of an alkanethiol having a terminal primary amine, hydroxyl or thiol group; and (b) converting sulfide linkages in the spacer groups to sulfoxide linkages. In selected embodiments, submonomer (i) is acrylic acid or an activated derivative thereof, and submonomer (ii) is an alkanethiol having a terminal primary amine, e.g. 2-aminoethanethiol, 2-hydroxyethanethiol, or 1,2-ethanedithiol.

Another method of preparing a solid support derivatized with hydrophilic spacer groups comprises: (a) synthesizing a spacer group on an acrylamide-derivatized solid support, by (i) reacting the thiol ftunctionality of a hydroxyalkanethiol with the acrylamide; and repeating the steps of: (ii) converting the hydroxyl functionality of the reacted hydroxyalkanethiol to a leaving group, and (iii) reacting the thiol functionality of a hydroxyalkanethiol with the leaving group; and (b) converting sulfide linkages in the spacer groups to sulfoxide linkages. Either of these methods may further comprise converting sulfide linkages in the spacer group to sulfoxide linkages and/or attaching ligation moieties to the free termini of the spacer groups. In selected embodiments, the solid support is amine-derivatized; in a further embodiment, the amine of the amine-derivatized support is attached to a ligation moiety, such as described above, and the amine is cleavable from the support.

In another aspect, the invention provides a hydrophilic spacer group-molecule conjugate having the structure:

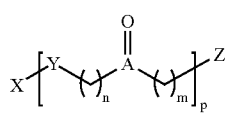

where Y is NH, O, or S, and is preferably NH; each of m and n is independently 2 to 6; A is S or Se, and is preferably S; p is 1 to 100, and preferably 2 to 25; one of X and Z is a terminating group or ligation moiety, and the other is a molecule selected from a peptoid, a peptide, an oligonucleotide, and an oligosaccharide, joined to the spacer group via an optional linking group. In one embodiment, the molecule is a peptoid. In one embodiment, n=m=2.

The ligation moiety which may be represented by X or Z typically comprises a functional group selected from the group consisting of: thiol, disulfide, hydroxyl, amino, carboxylic acid, thioester, thiocarboxylic acid, aldehyde, hydrazine, hydrazide, 3-mercapto-1,2-propanediyl, aminooxyacetyl, N-(2-thioethyl)amino, N-(2-hydroxyethyl)amino, 2-bromo amino acid, biotin, and protected derivatives thereof.

In selected embodiments of the conjugate, the peptoid has the general formula I:

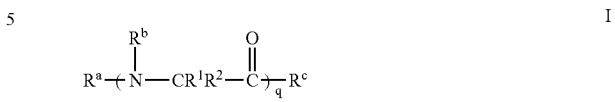

where $R^a$ is selected from the group consisting of alkyl, aryl, aralkyl, aralkenyl, and aralkynyl, any of which may be substituted with one or more groups W, hydrogen, —OH, —SH, —COOH, sulfonyl, and a lipid moiety wherein the lipid moiety may be conjugated to a linker moiety, each $R^b$ is independently selected from the group consisting of alkyl, aryl, aralkyl, aralkenyl, and aralkynyl, any of which may be substituted with one or more groups W, and hydrogen, where at least one group $R^b$ is not hydrogen;

$R^c$ is selected from the group consisting of alkyl, aryl, aralkyl, aralkenyl, and aralkynyl, any of which may be substituted one or more groups W, hydrogen, —OH, —SH, —NH$_2$, —NHR, —NH(C=O)R, where R is lower alkyl; sulfonyl, hydrazine, and a lipid moiety, wherein the lipid moiety may be conjugated to a linker moiety;

$R^1$ and $R^2$ are independently selected from hydrogen, lower alkyl, and lower alkoxy;

W is selected from hydroxy, alkoxy, amino, guanidino, amidino, alkylamino, alkylthio, halogen, nitro, cyano, keto, aldehyde, carboxylic acid, carboxylic ester, carboxylic amide, sulfonic acid and sulfonic ester; and q is an integer selected from 2 to about 50.

In selected embodiments of the conjugates, each $R^1$ and $R^2$ in the peptoid is hydrogen. In further embodiments, at least one $R^b$ in the peptoid includes a group which is cationic at physiologically relevant pH, and at least one $R^b$ is uncharged at physiologically relevant pH.

In another aspect, the invention provides a solid phase support derivatized with at least one hydrophilic spacer group having the structure:

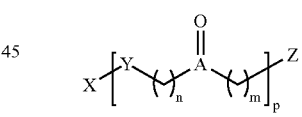

where Y is NH, O, or S, and is preferably NH; each of m and n is independently 2 to 6; A is S or Se, and is preferably S; p is 2 to 100, preferably 2 to 25; one of X and Z' is a terminating group, a ligation moiety, or a molecule selected from a peptoid, a peptide, and an oligonucleotide, and an oligosaccharide, joined to the spacer group via an optional linking group, and the other is the solid phase support. The support may be, for example, a bead or a planar surface. In one embodiment, n=m=2. The ligation moiety which may be represented by X or Z' typically comprises a functional group selected from the group consisting of: thiol, disulfide, hydroxyl, amino, carboxylic acid, thioester, thiocarboxylic acid, aldehyde, hydrazine, hydrazide, 3-mercapto-1,2-propanediyl, aminooxyacetyl, N-(2-thioethyl)amino, N-(2-hydroxyethyl)amino, 2-bromo amino acid, biotin, and protected derivatives thereof.

In related aspects, the invention provides kits useful for preparing a solid support derivatized with a plurality of molecules, comprising a spacer-derivatized solid phase support as described above, where one of group X or Z' is a ligation moiety, and the other is the solid phase support, and a plurality of molecules selected from peptoids, peptides, oligonucleotides, and oligosaccharides, each containing a ligation moiety effective to react with the ligation moiety X or Z' to form a stable linkage. In selected embodiments, the molecules are peptoids and/or constitute a combinatorial library.

In another aspect, the invention provides a method of synthesizing a branched peptoid. The method comprises: (a) synthesizing a peptoid chain on an amine-derivatized solid support, by repeating alternating addition of (i) an acyl submonomer bearing an α-leaving group and (ii) a primary amine submonomer, wherein at least one such primary amine submonomer is a diamine, having one free primary amine and one primary or secondary amine protected with a protecting group, such as p-nitrophenethyloxycarbonyl (NPEOC), which is not removed under the conditions of such synthesizing; (b) capping the free terminus of the peptoid chain; (c) removing the protecting group to produce a free primary or secondary amine; and (d) synthesizing a peptoid chain on the free amine of (c).

In a related aspect, the invention provides a method of preparing a library of disulfide-linked peptoids. This method comprises: (a) providing a plurality of solid support bound-peptoids, wherein each peptoid is derivatized with a thiol group, (b) providing a second plurality of solid support bound-peptoids, wherein each peptoid is derivatized with an activated disulfide; (c) contacting the first and second pluralities; and (d) cleaving the peptoids from the solid supports, under conditions effective to form disulfide-linked peptoid dimers. The second plurality may be provided by reacting a library of solid-support bound peptoids, each derivatized with a thiol or protected thiol group, with o-nitrosulfenyl chloride. Another method of preparing a library of disulfide-linked peptoids comprises: (a) providing a plurality of solid support bound-peptoids, wherein each peptoid is derivatized with a trityl sulfide (S-trityl) group, and (b) treating the solid support bound-peptoids with a reagent effective to cleave the trityl group and form disulfide-linked peptoid dimers. In one embodiment of this method, the reagent is iodine, and the peptoids remain bound to the support. In another embodiment, the reagent is TFA/MeSiCl$_3$, and the peptoids are cleaved from the support.

All of these methods provide means of synthesizing useful conjugates of biologically active, or potentially active, molecules, with moieties such as linkers, solid supports, spacers, or other molecules, entirely by solid phase synthesis. The syntheses are readily amenable to automation. These and other objects and features of the invention will become more fully apparent when the following detailed description of the invention is read in conjunction with the accompanying drawings.

DETAILED DESCRIPTION OF THE INVENTION

I. Definitions

Figure 1:
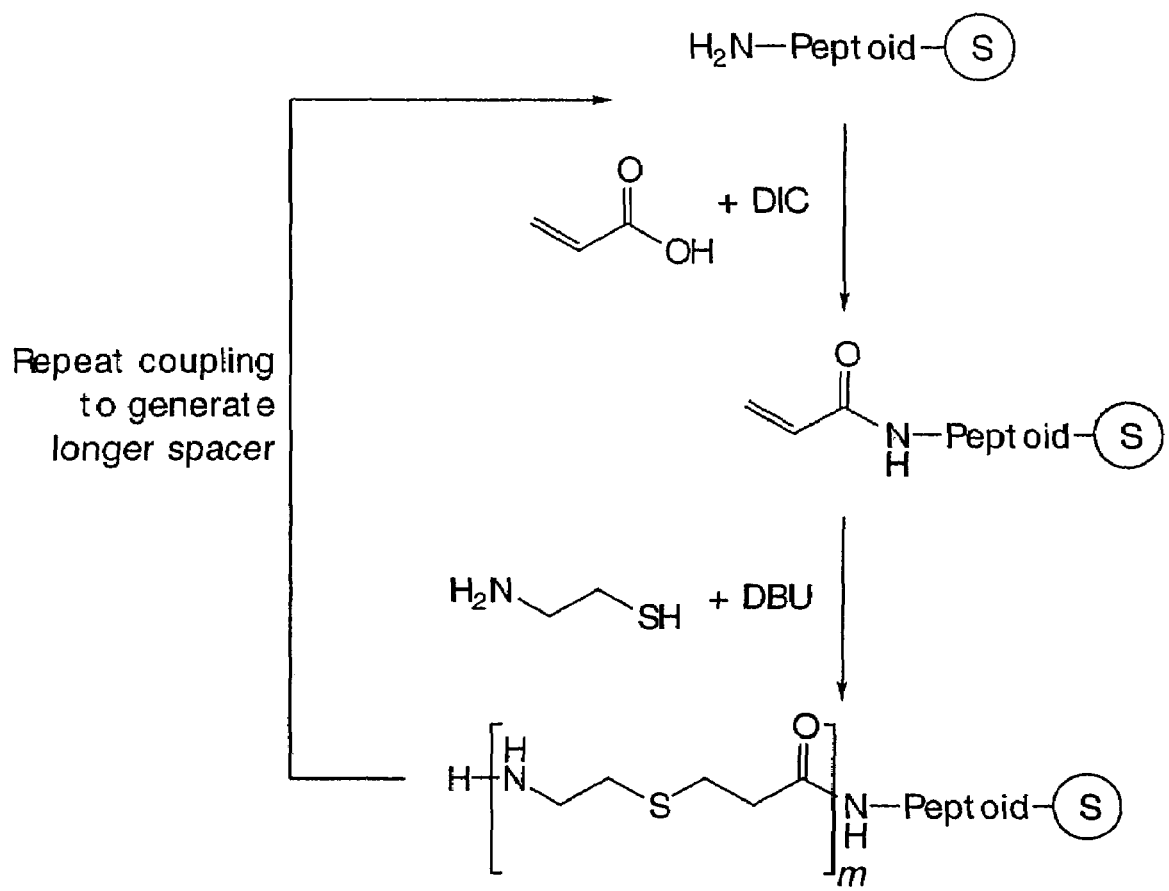
FIG. 1 shows a synthetic scheme for attaching a spacer group to a molecule by a submonomer route.

The terms below have the following meanings unless indicated otherwise.

A "peptoid" is a poly(N-substituted amide), preferably a poly(N-substituted glycine), as described, for example, in PCT Publications WO 94/06451, WO 98/06437, WO 99/08711, and U.S. Pat. No. 5,877,278 (Zuckermann et al.). For preparation of peptoids, see these references as well as: Bartlett, Santi et al. 1991; Horwell, Pritchard et al. 1992; Haenel 1994; Zuckermann and Kerr 1994; Hadas and Hornik 1995; Desai, Nuss et al. 1996; Kobylecki and Gardner 1996; Ng, Aarne et al. 1996; Zuckermann, Siegmund et al. 1998; Zuckermann, Troung et al. 1998; Zuckermann, Chinn et al. 1998; Zuckermann, Goff et al. 1999; 2000; and DE Utility Model Pubn. No. 20005738, all cited above, each of which is incorporated herein by reference in its entirety and for all purposes.

One class of peptoids has the general formula I:

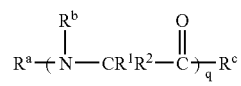

where $R^a$ is selected from the group consisting of alkyl, aryl, aralkyl, aralkenyl, and aralkynyl, any of which may be substituted with one or more groups W, hydrogen, —OH, —SH, —COOH, sulfonyl, and a lipid moiety, wherein the lipid moiety may be conjugated to a linker moiety, each $R^b$ is independently selected from the group consisting of alkyl, aryl, aralkyl, aralkenyl, and aralkynyl, any of which may be substituted with one or more groups W, and hydrogen, where at least one group $R^b$ is not hydrogen;

$R^c$ is selected from the group consisting of alkyl, aryl, aralkyl, aralkenyl, and aralkynyl, any of which may be substituted with one or more groups W, hydrogen, —OH, —SH, —NH$_2$, —NHR, —NH(C=O)R, where R is lower alkyl; sulfonyl, hydrazine, and a lipid moiety, wherein the lipid moiety may be conjugated to a linker moiety;

$R^1$ and $R^2$ are independently selected from hydrogen, lower alkyl, and lower alkoxy;

W is selected from hydroxy, alkoxy, amino, guanidino, amidino, alkylamino, alkylthio, halogen, nitro, cyano, keto, aldehyde, carboxylic acid, carboxylic ester, carboxylic amide, sulfonic acid and sulfonic ester; and q is an integer selected from 2 to about 50.

In selected embodiments, $R^c$ is selected from —$NH_2$, —NHR, and —NH(C=O)R, where R is lower alkyl. When each of $R^1$ and $R^2$ is hydrogen, the molecule is a poly(N-substituted glycine). With respect to the peptoid N-side chains, in selected embodiments, at least one $R^b$ includes a group which is cationic at physiologically relevant pH (e.g. aminoalkyl, quaternary ammonium, guanidino, amidino, imidazolium, pyridinium), and at least one $R^b$ is uncharged at physiologically relevant pH. Examples include alkyl and aralkyl; specific examples are isopropyl and (p-methoxyphenyl) ethyl. Cationic or neutral side chains of naturally occurring acids may also be used. Preferably, each group $R^b$ includes either a cationic or uncharged group. A particularly preferred structure includes a repeating sequence of one cationic group and two uncharged groups at $R^b$.

A "lipid moiety" is a hydrophobic moiety having a substantial hydrocarbon component, preferably comprising a group selected from $C_{10}$-$C_{50}$ branched or unbranched alkyl, alkenyl or alkynyl, $C_{14}$-$C_{50}$ aryl, aralkyl, aralkenyl, or aralkynyl, or a steroid nucleus. Examples of lipid moieties include dialkyl- or dialkenyl-phospholipids, such as phosphatidyl cholines, phosphatidyl ethanolamines, and phosphatidyl inositols, glycolipids, such as cerebrosides and gangliosides, fatty diacylglycerides, glycosylglycerides, sphingolipids, and steroids, including sterols.

A "lipitoid" is a lipid-substituted peptoid, e.g. a compound of formula I above where $R^a$ comprises a lipid moiety. A "cholesteroid" is a cholesterol-substituted peptoid, e.g. a compound of formula I above where $R^a$ comprises a cholesteryl moiety. While cholesterols are preferred, further disclosure of steroids useful for incorporating into steroid-peptoid conjugates is found in PCT publication WO 97/46223 (Fasbender et al.) and corresponding U.S. Pat. No. 5,935,936, which are hereby incorporated by reference. As used herein, the term "peptoid" encompasses lipitoids and cholesteroids.

The term "peptide" refers to a compound made up of a single chain of D- or L-amino acids or a mixture of D- and L-amino acids joined by peptide bonds, typically up to about 50 amino acids in length.

The term "oligonucleotide" refers to a oligomeric molecule having a backbone which supports bases capable of hydrogen bonding in a sequence specific manner to typical nucleic acids (e.g., single-stranded RNA, double-stranded RNA, single-stranded DNA or double-stranded DNA), where the oligomer backbone presents the bases in a manner to permit such hydrogen bonding. The term includes oligomers with non-standard nucleotide backbones, for example, backbones formed using phosphorothioate or phosphorodiamidate chemistry, or with modified bases.

An "oligosaccharide" refers to a molecule made up of two or more monosaccharide units joined by anomeric linkages. Oligosaccharides may be linear or branched. For purposes of solid-phase synthesis, particularly combinatorial syntheses, molecules having up to twelve monosaccharide units, more typically up to six, and frequently two or three, are generally contemplated. See, for example, the review article by Seeberger (*Chem. Rev.* 100:4349, 2000).

"Alkyl" refers to a fully saturated acyclic monovalent radical containing carbon and hydrogen, which may be branched or a straight chain. Examples of alkyl groups are methyl, ethyl, n-butyl, t-butyl, n-heptyl, and isopropyl. "Alkenyl" refers to an acyclic monovalent radical containing carbon and hydrogen, which may be branched or a straight chain, and which contains at least one carbon-carbon double bond. The alkenyl group may be monounsaturated or polyunsaturated. Similarly, "alkynyl" refers to such a radical having at least one carbon-carbon triple bond. "Lower" alkyl (alkenyl, alkynyl, alkoxy, etc.) refers to a group having 1 to 6 carbons, preferably 1 to 4 carbons.

"Aryl" refers to a substituted or unsubstituted monovalent aromatic radical having a single ring (e.g., benzene) or two or three condensed rings (e.g., naphthyl; phenanthryl). Groups having a single ring (monocyclic) or two condensed rings (bicyclic) are generally preferred, with monocyclic groups being particularly preferred. The term includes heteroaryl groups, which are aromatic ring groups having one or more nitrogen, oxygen, or sulfur atoms in the ring, such as furan, pyrrole, pyridine, imidazole, and indole. By "substituted" is meant that one or more ring hydrogens in the aryl group is replaced with a non-hydrogen group, preferably selected from halogen, lower alkyl, lower alkoxy, nitro, amide, tertiary amino, hydroxy, and halo(lower alkyl).

"Aralkyl" refers to an alkyl, preferably lower alkyl, substituent which is further substituted with an aryl group; one example is a benzyl group. Similarly, "aralkenyl" and "aralkynyl" refer to alkenyl or alkynyl substituents further substituted with an aryl group.

A "combinatorial library", in general, is a collection of compounds based upon a core structure which has independently variable substituents, functional groups or other structural elements. For the range of chemical moieties selected for each of the independently variable elements, compounds containing all possible permutations of those elements may be present in the library. The method for preparing a combinatorial library is preferably such that all or any combination of diverse members of the library can be synthesized simultaneously. The peptoid libraries discussed herein typically contain 2 to about 1000, preferably about 10 to 500, different-sequence peptoids. Such libraries can be prepared by applying known combinatorial synthesis strategies to the synthesis of peptoids, described further below. See, for example, Thompson et al., "Synthesis and Applications of Small Molecule Libraries," *Chem. Rev.* 96:55-600 (1996); Terrett et al., "Combinatorial Synthesis: The Design of Compound Libraries and Their Application to Drug Discovery," *Tetrahedron* 51(30):8135-8173 (1995) and Bunin, B., "Combinatorial Index," Acad. Press (1998). In particular, particle-supported combinatorial libraries can be prepared containing a large number of polymers using the methods described in WO 99/58476 and corresponding U.S. Patent Application, Ser. No. 60/084,843, which is incorporated herein by reference in its entirety and for all purposes.

A "trityl" protecting group, as used herein, includes trityl-based protecting groups in which one or more of the phenyl rings are substituted, e.g. by methoxy.

Abbreviations:
FMOC: 9-fluorenylmethoxycarbonyl
Boc: t-butoxycarbonyl
Tr: trityl (triphenylmethyl)
TFA: trifluoroacetic acid
TIPS: triisopropylsilyl
DBU: diazabicyclo[5.4.0]undecane
DTT: dithiothreitol
DIC: diisopropycarbodiimide
TMOF: trimethylorthoformate

II. Solid Phase Synthesis of Conjugates

The present invention provides, in one aspect, methods of preparing various conjugates, particularly peptoid-containing conjugates, by a submonomer synthesis approach. The versatility and convenience of the submonomer approach in preparing peptides has been described in, for example, U.S. Pat. Nos. 5,831,005 and 5,977,301; see also Murphy et al., *Proc. Natl. Acad. Sci. USA* 95:1517 (1998) and Huang et al., *Chem. & Biol.* 5:345 (1998), and references therein. The present methods allow various peptoid-containing conjugates to be synthesized entirely in the solid phase. The conjugates include a peptoid linked to one or more of the following, in varying sequence: a spacer group, a ligation moiety, a solid support, and/or another molecule selected from, for example, a peptide or protein, an oligonucleotide, an oligosaccharide, or another peptoid.

The submonomer method can also be used to form a conjugate consisting of a hydrophilic spacer group linked to one or more of a ligation moiety, a solid support, and a molecule such as a peptide, peptoid, oligosaccharide or oligonucleotide, in varying sequence. As described further below, the hydrophilic spacer groups are advantageous in that they minimize nonspecific binding of peptoids or biomolecules such as proteins, peptides, oligosaccharides and oligonucleotides.

Such conjugates have a variety of applications. For example, peptoids can be conjugated to nucleic acid oligomers for enhanced delivery (see e.g. PCT Publications WO 98/06437 and WO 99/08711) in, for example, antisense applications. Peptoids having an alkyl spacer and a thiol functionality, synthesized by the methods described herein and derivatized with the ligation moiety TrS-$(CH_2)_{10}$—COOH, are useful in forming Self-Assembling Monolayers (SAM) when spotted directly onto gold and other metal surfaces. In certain applications, a hydrophilic spacer group, as described herein, is particularly useful. For example, peptoids can be conjugated to a planar surface for use in solid-phase screening of binding of biomolecules. Conjugation of ligand molecules, including peptoids, to a solid phase which is a chromatographic material can be used to prepare affinity chromatographic materials. In these cases, the hydrophilic spacer provides spatial separation of the molecule with potential binding activity (e.g. the peptoid) and the solid support, and it itself resists nonspecific absorption of proteins or other biomolecules from solution.

A. Submonomer Syntheis of Spacer Group-Containing Conjugates

In one embodiment, a spacer group-molecule conjugate is prepared, where the molecule is preferably selected from a peptoid, a peptide, an oligonucleotide, and an oligosaccharide.

A1. Sulfide- and Sulfoxide-Containing Spacer Groups

One method of forming a spacer group by a stepwise submonomer route is as follows (see FIG. 1). An amine, hydroxyl or thiol functionality on the molecule is first reacted with a first submonomer consisting of acrylic acid, an alkanoic acid bearing a terminal leaving group, or an activated derivative thereof. The "alkanoic acid bearing a terminal leaving group" may include, for example, an α-halo acetic acid, β-halo propanoic acid, 2-(methanesulfoxy)acetic acid, etc. Lower alkyl acids such as these are preferred for purposes of hydrophilicity. Activated derivatives of such acids include esters, such as N-succinimidyl esters, and other activated carboxyl functionalities, such as are frequently employed in peptide synthesis, formed by reaction with such reagents as DCC (dicyclohexylcarbodiimide) or CDI (1,1'-carbonyl diimidazole). FIG. 1 illustrates reaction of acrylic acid in the presence of the activating reagent DIC (diisopropylcarbodiimide).

This first addition forms an amide, ester, or thioester linkage between the molecule and first submonomer. For purposes of stability, amide linkages are generally preferred.

A second submonomer, consisting of an alkanethiol having a terminal primary amine, hydroxyl or thiol group, is then reacted with the double bond (when an acrylic acid is employed) or leaving group (when an alkanoic acid is employed) of the first submonomer. Exanples of second submonomers include 2-aminoethanethiol, 3-aminopropanethiol, 2-hydroxyethanethiol, and 1,2-ethanedithiol. Although submonomers having longer alkyl chains can be used, shorter chains are again preferred, in order to provide greater hydrophilicity. However, any alkanethiol having suitable hydrophilicity as determined using methods and materials known to those having skill in the organic chemical synthesis arts can be used. The alkyl chain may also include intervening ether linkages.

The nucleophilic thiol moiety of the second submonomer adds to the conjugated double bond or displaces the leaving group of the first submonomer, forming a sulfide linkage. The terminal primary amine, hydroxyl or thiol group may then be reacted with another "first submonomer" (i.e. acrylic acid, an alkanoic acid bearing a terminal leaving group, or an activated derivative thereof), and the sequence is repeated, as shown, to produce the desired-length spacer group. Preferably, at least one repetition is performed, and additional repetitions are generally useful, such that linker chains up to about 300 atoms in length, preferably from about 15 to about 150 atoms in length, are prepared. In some cases, even longer linkers may be useful.

Figure 2:
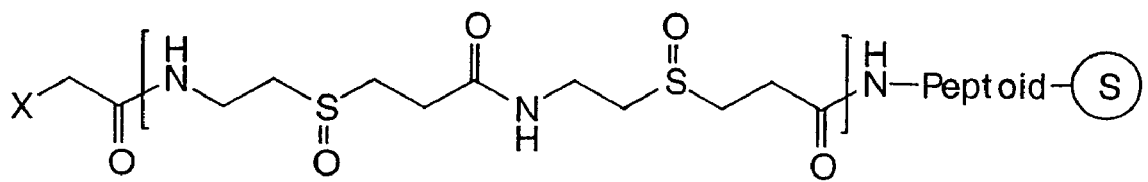
FIG. 2 shows one embodiment of a solid support-peptoid-hydrophilic spacer-ligation moiety conjugate, where the ligation moiety is represented by X.

Conversion of the sulfide linkages of the above-described spacer group to sulfoxides provides a spacer group having increased hydrophilicity and much reduced binding interactions with proteins. Thus, following the synthesis of the spacer, or the spacer-containing conjugate, the sulfide linkages in the spacer are oxidized to give the more hydrophilic sulfoxide linkages, resulting in a spacer which is effective to resist adsorption of proteins and other biomolecules from solution. This conversion can be accomplished on the solid-support bound construct by periodate oxidation. FIG. 2 shows one embodiment of a support-peptoid-hydrophilic spacer-ligation moiety conjugate, where the ligation moiety is represented by X.

Figure 3:
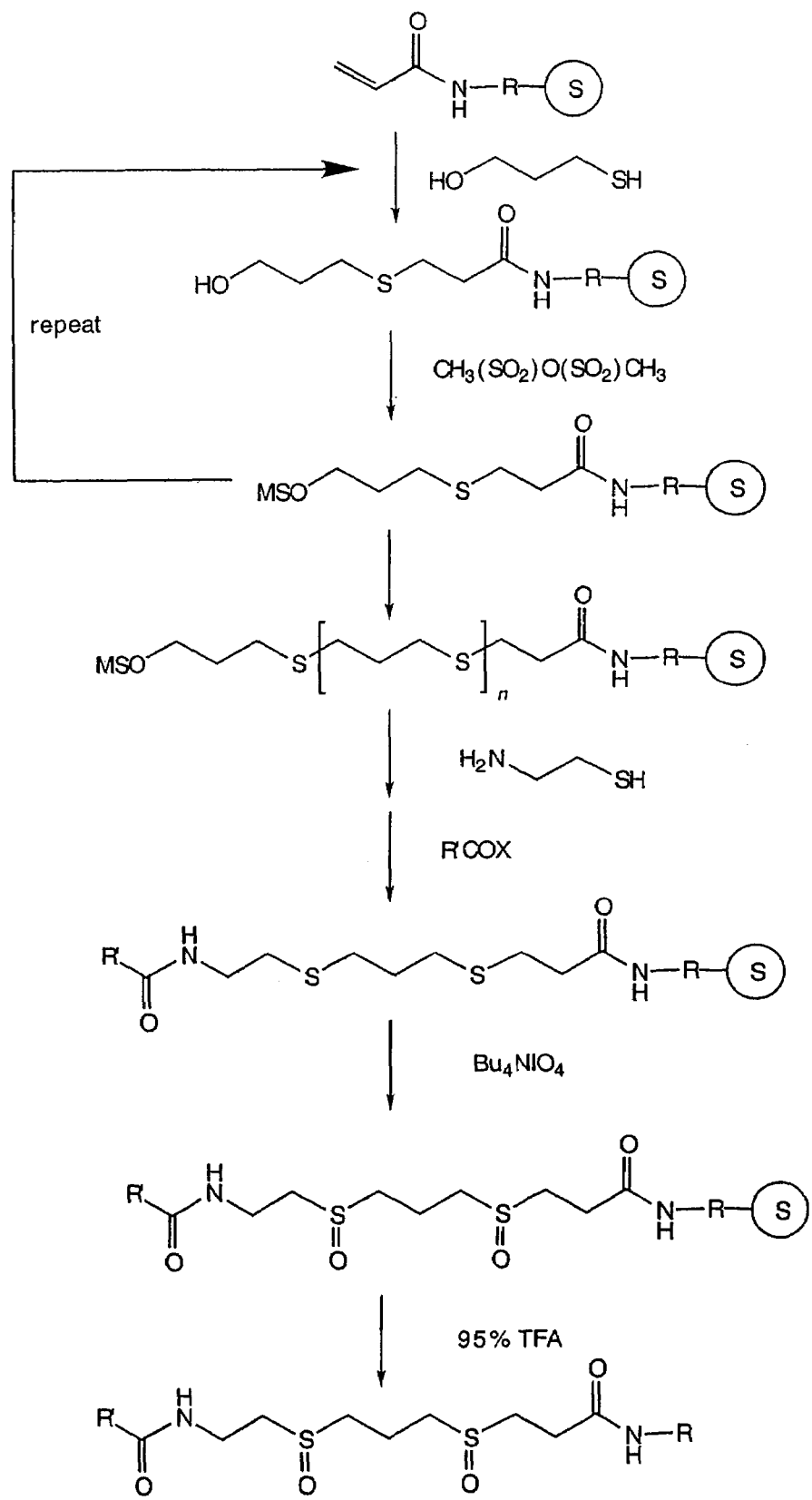
FIG. 3 shows a method for synthesis of a sulfoxide-containing spacer group.

Alkyl sulfoxide-based linkers may also be prepared by the following stepwise route (FIG. 3): The N-terminus of a peptoid is converted to the acrylamide derivative, and an alkanethiol having a terminal hydroxy group, e.g. 3-mercaptopropanol, is added, to give, in this case, the corresponding S-(3-hydroxypropyl)3-mercaptopropionamide derivative. To elongate the spacer molecule, the following two steps are repeated: a) conversion of the free hydroxy group to the methanesulfonyl ester, using methanesulfonyl chloride or methanesulfonic anhydride, and b) further addition of the alkanethiol in the presence of DBU. During the last cycle, a mercapto monomer containing a suitable secondary functionality useful for further synthesis, e.g. 2-cysteamine, may be added to provide an amine terminus. The sulfide linkages may be converted to sulfoxide linkages for increased hydrophilicity, as described above.

Figure 4:
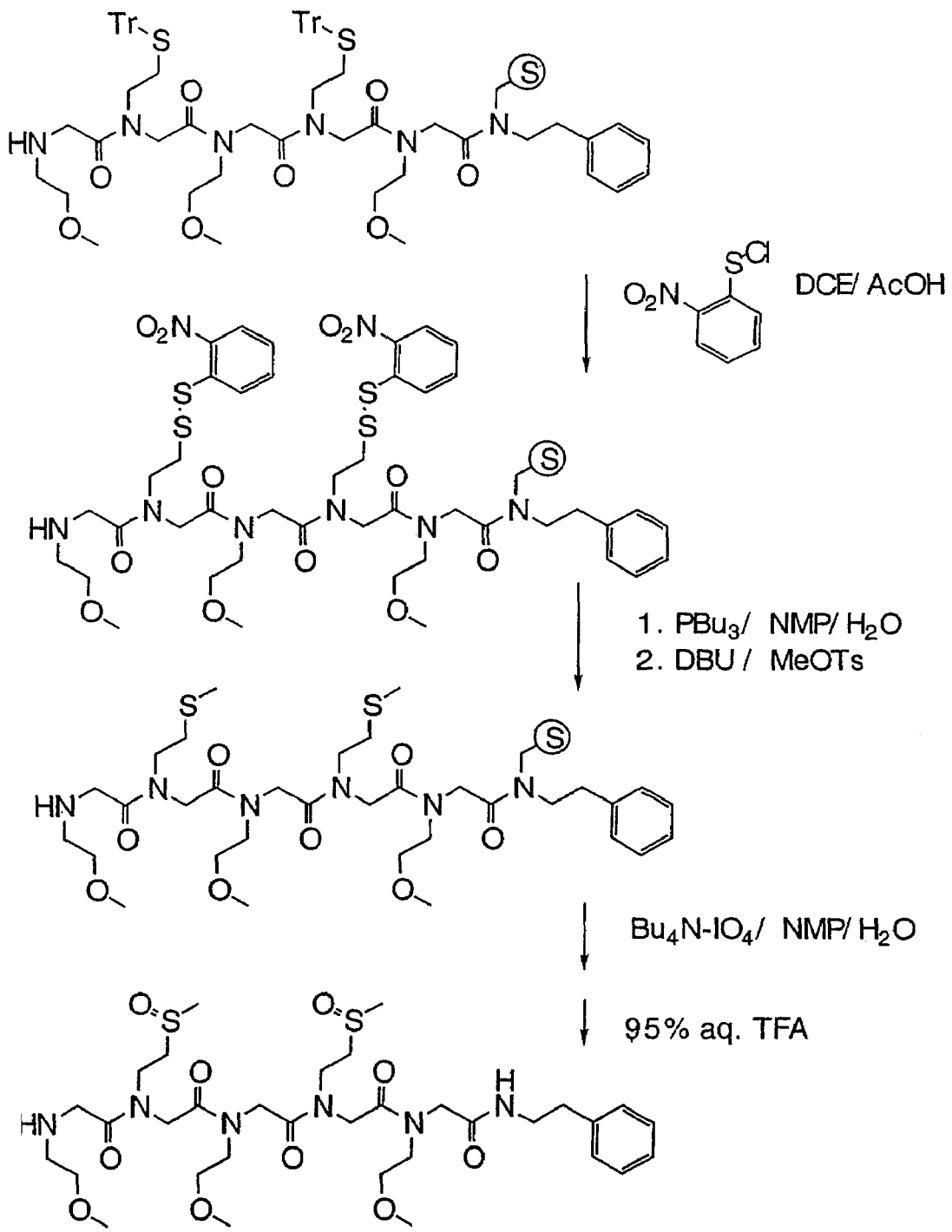
FIG. 4 illustrates attachments of sulfoxide-containing side groups to a peptoid.

Sulfoxide side-groups may also be incorporated into peptoids, e.g. by the method shown in FIG. 4, to reduce nonspecific protein binding. A sulfoxide side chain can be incorporated by employing a protected thioalkyl primary amine, such as Tr-S—$CH_2CH_2$—$NH_2$, as the amine submonomer in a standard peptoid synthesis as described above. The trityl group is removed by treatment with o-nitrophenylsulfenyl chloride followed by reduction (with $PBu_3$, DTT, or other suitable reductant) to give the free thiol, which is then methylated with Me-O—SO$_2$—R (R=p-toluene, methane) in the presence of DBU, to give a methionine-like side chain. The sulfide linkages are then oxidized with periodate.

A2. Other Spacer Groups

Other linkers may also be prepared by controlled stepwise synthesis in the solid phase. For example, Rose et al. (Rose, K. and Vizzavona, J., *J Am. Chem. Soc.* 121: 7034-7038, 1999) have described the stepwise solid phase synthesis of polyamide linkers of the form (NH—Y—NH—CO—X—CO)$_n$, containing a precise number of monomer units, where X and Y can be varied in at each step. These can be used as linking or scaffold groups for peptoids, peptides or other biomolecules.

Figure 5:
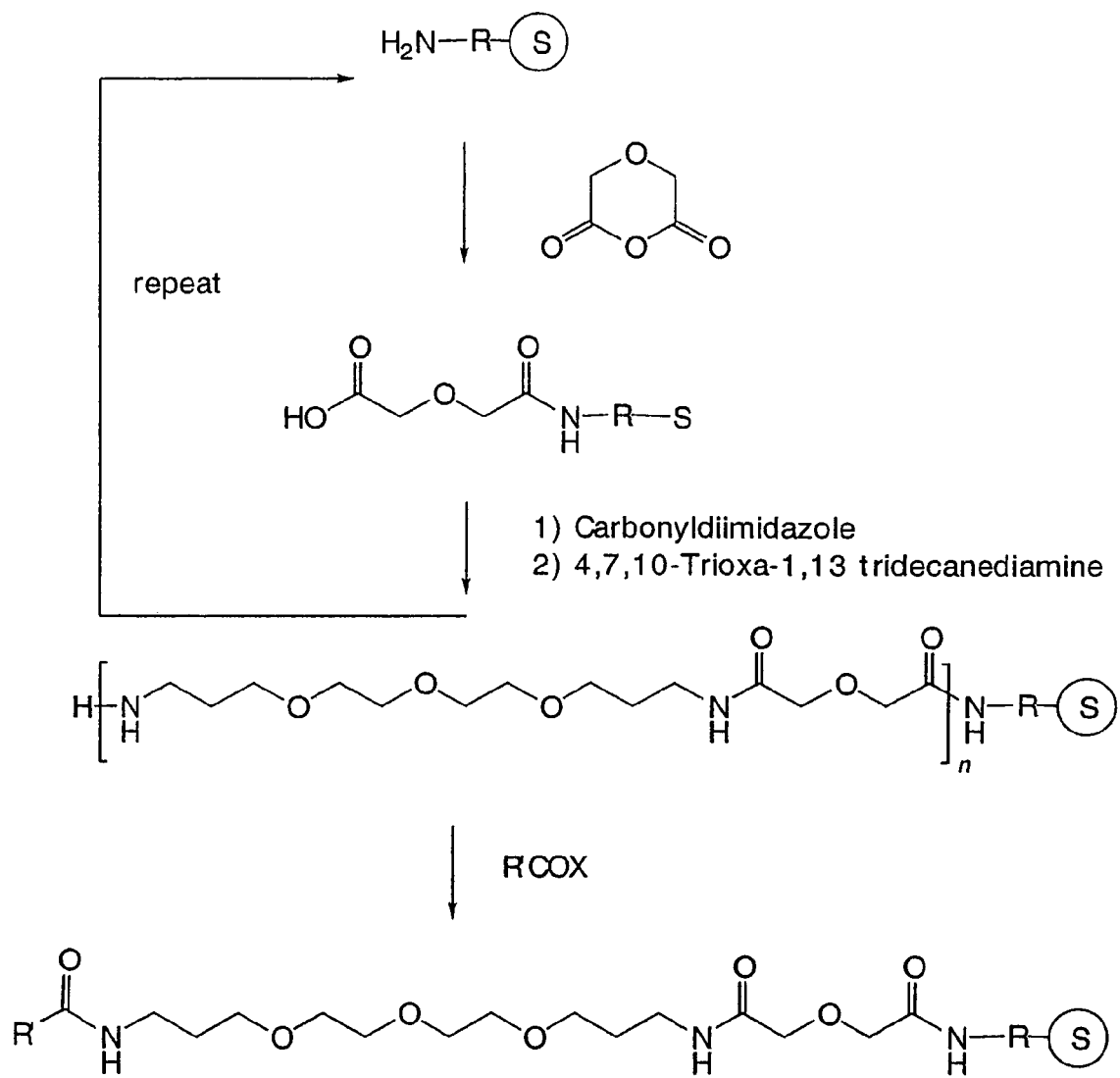
FIG. 5 shows a method for synthesis of a PEG spacer group.

Peptoid-PEG constructs can be designed to act as macromolecular prodrugs, can form part of long-circulating liposomes, and can be targeted to particular cells. A spacer containing PEG-like moieties may be prepared by stepwise solid phase synthesis as described in Example 5 and illustrated in FIG. 5. An amine-derivatized solid support, or solid support bearing a molecule such as a peptoid with a reactive amine functionality, is treated with (i) diglycolic anhydride in NMP containing N-methylimidazole, followed by (ii) 4,7,10-trioxa-1,13-tridecanediamine in NMP containing 0.5 M N-hydroxybenztriazole. Treatments (i) and (ii) are repeated as desired to construct a PEG spacer of the desired length. The spacer has the repeating subunit shown in the Figure. To introduce a cleavable site in the spacer, O,O-isopropylidine tartaric anhydride can be substituted for diglycolic anhydride in step (i). Deprotection of the diol and periodate oxidation results in cleavage. See Fruchart et al., *Tetrahedron Lett.* 40:6225-6228 (1999).

In one embodiment of the above conjugate syntheses, the molecule is attached to a solid phase support, and may itself be synthesized on the solid support by stepwise synthesis. When the molecule is a peptoid, it may be synthesized on an amine- or hydroxyl-derivatized solid support by repeating alternating addition of (i) an acyl submonomer bearing an α-leaving group and (ii) a primary amine submonomer, as described, for example, in U.S. Pat. Nos. 5,831,005 and 5,977,301.

Alternatively, the spacer may be synthesized on a solid support, followed by attachment of the molecule. The spacer is synthesized on an amine- or hydroxyl-derivatized, preferably amine-derivatized, solid support by repeating alternating submonomer addition, as described above, followed by attachment of the molecule. The molecule itself may be attached by stepwise solid phase synthesis. For example, a peptoid may be synthesized, attached to an amino, hydroxyl or thiol group of said spacer, by repeating alternating addition of (i) an acyl submonomer bearing an α-leaving group and (ii) a primary amine submonomer. Solid phase synthesis of peptides, oligonucleotides and oligosaccharides is well known in the art. (For a review of "Solid-Phase Oligosaccharide Synthesis and Combinatorial Carbohydrate Libraries", see P. H. Seeberger et al., *Chem. Rev.* 100(12):4349-4393 (2000).)

The submonomer method can also be used to form a conjugate consisting of a spacer group linked to one or more of a ligation moiety, a solid support, and a molecule such as a peptoid, peptide, oligonucleotide or oligosaccharide, in varying sequence.

In one embodiment, the conjugate has the form molecule-spacer group-conjugation partner. The spacer group provides a desired amount of spatial separation between the molecule, which is often a candidate to be screened for a biological activity, such as binding affinity, and the conjugation partner, which may be a solid support, peptoid, peptide or protein, or oligonucleotide.

B. Ligation Moieties

In one embodiment of the above conjugate syntheses, a ligation moiety is attached to a free terminus of the spacer group or molecule. This provides a molecule-spacer-ligation moiety or spacer-molecule-ligation moiety conjugate (see FIG. 6), where the molecule or spacer group may be further conjugated to a solid support.

In another embodiment, where an amine-derivatized solid support is employed, a ligation moiety is attached to the amine of the solid support. Cleavage from the support releases the terminus containing the ligation moiety (see FIG. 7).

Attachment of a chemoselective ligation moiety provides a means of further attaching the conjugate to a further partner. The ligation moiety comprises a functional group which is reactive towards a complementary group that is displayed on the conjugation partner and orthogonal to any reactive side chain groups present in the molecule. Preferably, reaction of the ligation moiety with the conjugation partner is sufficiently facile to be complete within approximately 15-20 minutes at millimolar or micromolar concentrations. An example is the average lifetime of a droplet (solvent DMSO:H$_2$O 1:1) deposited by a robotic array spotter, such as described in WO 99/58476, onto a surface.

A large number of chemical linking strategies, including the use of orthogonal functional groups or protecting groups, are known in the art. In preferred embodiments, the ligation moiety comprises a functional group selected from the group consisting of: thiol, carboxylic acid, thioester, thiocarboxylic acid, aldehyde, hydrazine, hydrazide, 3-mercapto-1,2-propanediyl, aminooxyacetamide, N-(2-thioethyl) aminoacetamide, N-(2-hydroxyethyl) aminoacetamide, 2-bromo amino acid, biotin, and protected derivatives thereof.

In general, chemoselective ligation employs a mutually reactive nucleophile-electrophile pair which react to form a linkage. Such linkages, and functional groups that can be reacted to form them, include thioether (reaction of thiol with maleimide or acrylamide), disulfide (activated disulfide with thiol), hydrazone (aldehyde or ketone with hydrazine or hydrazide) semicarbazone (aldehyde or ketone with semicarbazide), oxime (aldehyde or ketone with aminooxyacetyl), thiosemicarbazone (aldehyde or ketone with thiosemicarbazide), and thiazolidine (aldehyde and cystein; see below). Any of these functional groups can be provided in protected form, to be deprotected prior to conjugation. The ligation group can also include a biotin moiety, which will form a strong noncovalent linkage to a conjugation partner that displays avidin protein.

Ligation strategies described by Dawson et al. (*Science* 266(5186):776, 1994), Liu and Tam (*PNAS* 91:6584, 1994), Tam et al. (*PNAS* 92:12485, 1995), and Zhang and Tam (*Anal. Biochem.* 233(1):87, 1996) employ a two-step reaction sequence, where, in the first step, a stable covalent intermediate is formed between two segments, and, in the second step, an additional bond, frequently an amide bond, is spontaneously formed via an intramolecular acyl transfer. Examples include pseudoproline amide (thiazolidine) formation from reaction of an aldehyde and cysteine (Zhang et al.; Liu and Tam); carboxamide formation from reaction of a thioester and cysteine, termed "native chemical ligation", as described by Dawson et al., and carboxamide formation from reaction of a thiocarboxylic acid with S-activated cysteine or 2-bromo amino acid (Liu and Tam; Tam et al.).

B1. N-terminal Modifications

Figure 8:
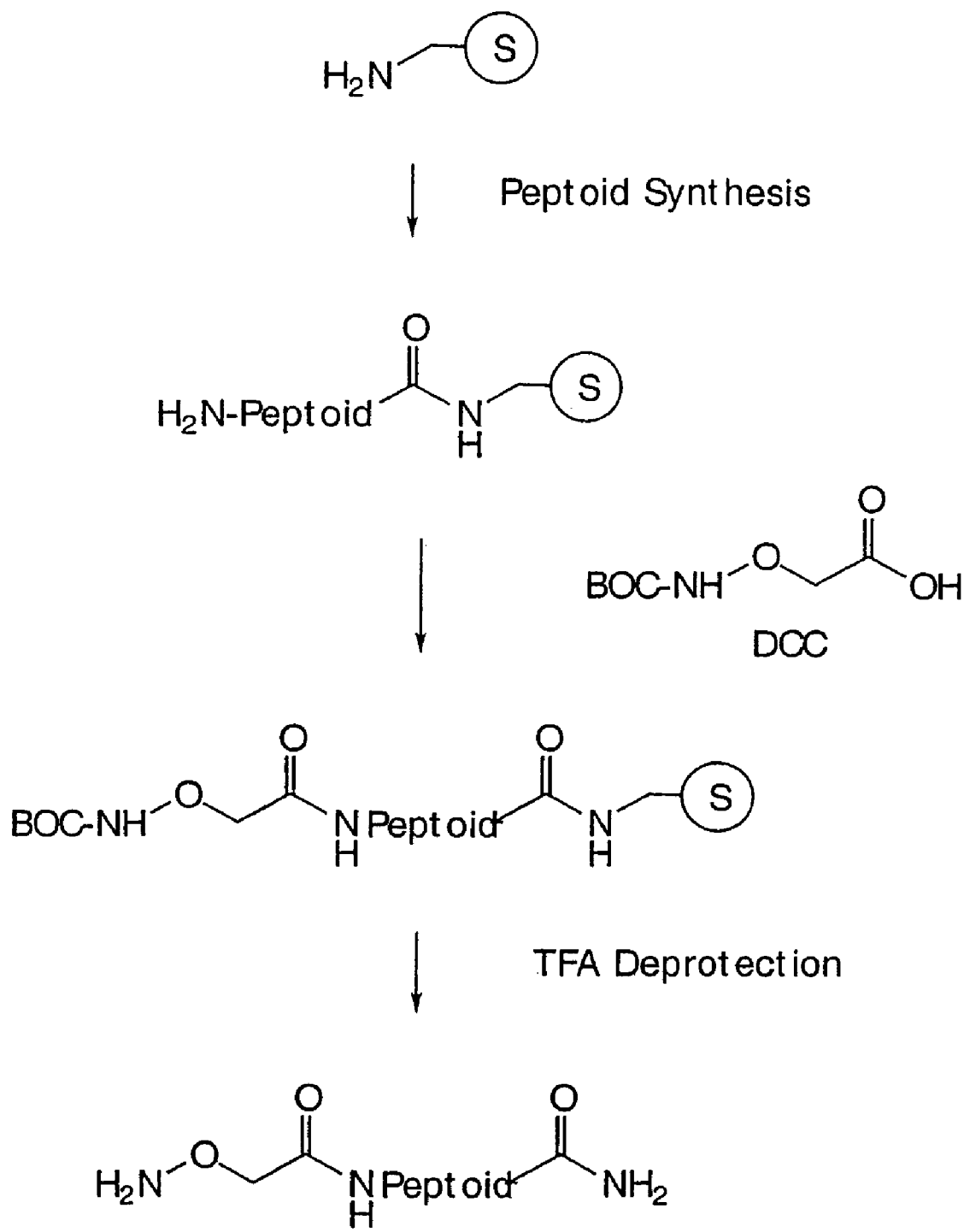
FIG. 8 illustrates N-terminal attachment of a ligation moiety to a support-bound peptoid, via direct coupling of a carboxylic acid containing the protected ligation moiety.

As stated above, in one embodiment, a ligation moiety is attached at the free terminus of a support bound molecule (e.g. peptoid, peptide, oligonucleotide, or oligosaccharide), spacer group or conjugate thereof. This is conveniently achieved by reacting a nucleophilic moiety at the terminus, typically an amine, with a carboxylic acid containing, in protected form, a reactive moiety such as a thiol, aminooxy, or hydrazino functionality. See, for example, FIG. 8, where the reactive moiety is an aminooxy group. As a further example, incorporation of serine followed by periodate oxidation gives a terminal aldehyde. Incorporation of cysteine gives a terminal 2-thioethylamino group that can be used in "native chemical ligation", described above.

Following are exemplary modified carboxylic acids that can be used for this purpose. Typically, n=1-10. The terminal functional groups can be deprotected with TFA after addition.

Boc—NH—O—$(CH_2)_n$—COOH (aminooxy)
Boc—NH—NH—CO—$(CH_2)_n$—COOH (hydrazino)
Tr—S—$(CH_2)_n$—COOH (thiol)

Figure 6:
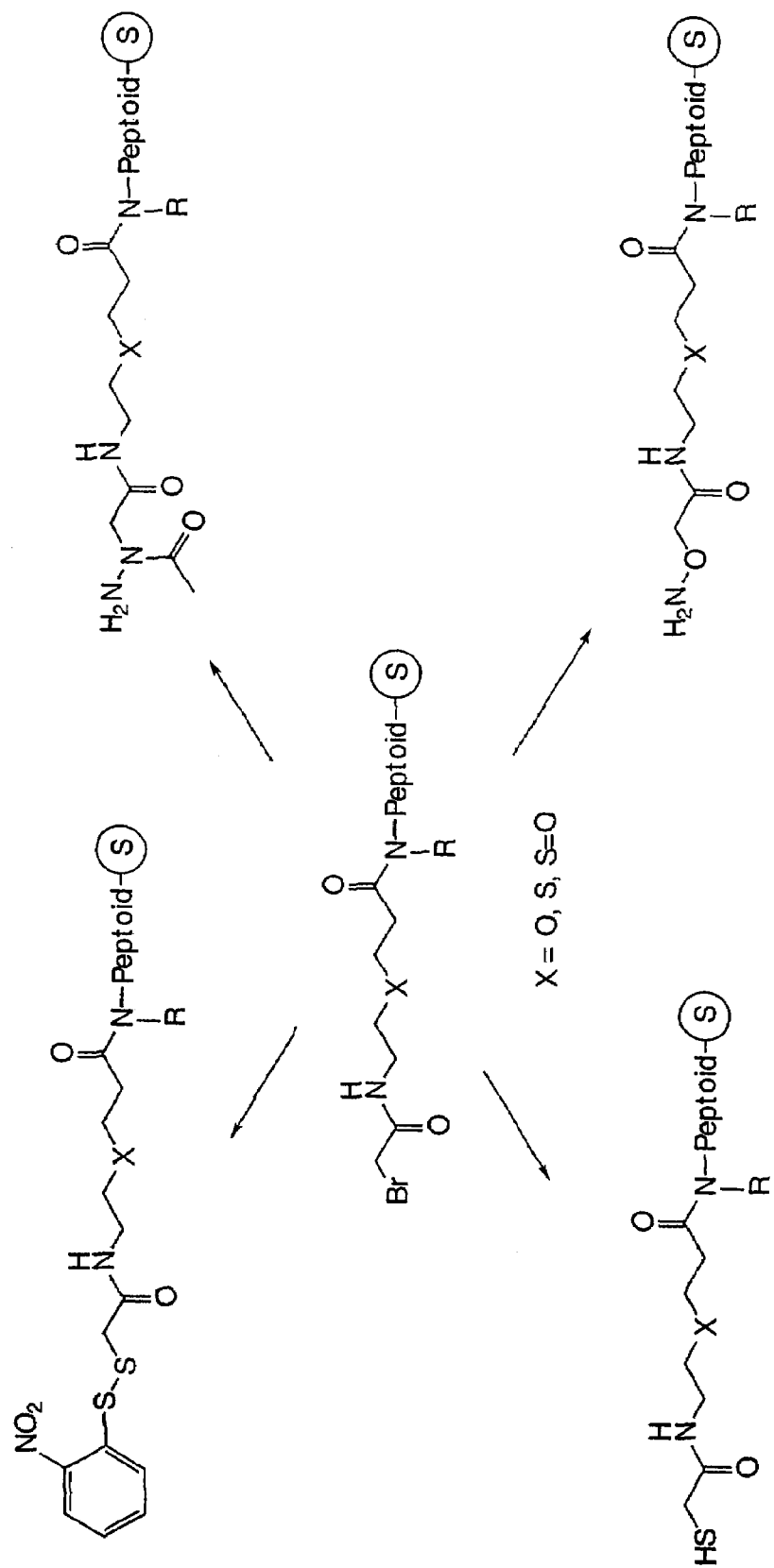
FIG. 6 illustrates N-terminal attachment of various ligation moieties to a peptoid-spacer conjugate, via displacement of a leaving group at the spacer terminus.

N-terminal chemoselective ligation moieties may also be introduced by bromoacetylation of the N-terminus to form an α-bromoacetamide, followed by displacement of the bromine with an active species, such as those outlined below. Several examples are illustrated in FIG. 6.

a) Addition of S-trityl-thioethylamine or O-TIPS-hydroxyethylamine results in a terminal N-(2-thioethyl)aminoacetamide or N-(2-hydroxyethyl)aminoacetamide. Either of these can be coupled to another molecule terminating in a thioester or aldehyde to form an amide bond, using a "native peptide ligation" scheme (see references cited above).

b1) Displacement with thiolacetic acid ($CH_3COSH$) or potassium O-ethyldithiocarbonate ($CH_3CH_2OCS_2K$) and treatment with a primary alkylamine produces a spacer that terminates in a free thiol (i.e., —NH—CO—$CH_2$Br→—NH—CO—$CH_2$—S—CO—$CH_3$ or NH—CO—$CH_2$—S—CS—OEt→—NH—CO—$CH_2$—SH). The bromide can also be converted to the thiol by using $(BnEt_3N)_2MoS_4$ to produce a disulfide (—S—S—) which is then reduced to free —SH using $PBu_3$ or another suitable reductant (see Prabhu et al., *Angew. Chem. Int. Ed* 39:4316-4319, 2000).

b2) Displacement with the sodium salt of tert-butylmercaptan produces the tert-butyl protected thiol, which is stable to TFA deprotection. Treatment of this group with o-nitrophenylsulfenyl chloride/acetic acid generates the activated o-nitrophenyl disulfide.

c) Displacement with N-hydroxy-succinimide in the presence of strong base (e.g. DBU) and subsequent treatment with hydrazine produces a spacer that terminates in a free aminooxyacetyl (—NH—$COCH_2$—O—$NH_2$) functionality.

d) Displacement with BOC—NH—$NH_2$ and standard TFA deprotection results in a terminal hydrazino (—NH—$COCH_2$—$NHNH_2$) functionality.

e1) Displacement with BOC—NH—$NH_2$ and acetylation prior to TFA deprotection results in a terminal hydrazido (—CO—$NHNH_2$) functionality.

e2) Addition of $C(CH_2O—CO—CH_2CH_2—SH)_4$ results in a terminal ester which, on treatment with hydrazine, also forms a hydrazide group.

f) Addition of HOOC—$CH_2CH_2$—SH produces a terminal free carboxylic acid group.

g1) Addition of DTT and oxidation with sodium periodate, prior to TFA deprotection, produces a terminal aldehyde, with concomitant oxidation of sulfide linkages in the spacer group to sulfoxides.

g2) Coupling of N-FMOC-serine and removal of FMOC provides a terminal aldehyde functionality after periodate oxidation.

h) A dithiothreitol-terminated peptoid, made by addition of DTT to a terminal bromoacetylated or acrylated peptoid, produces a spacer which contains a diol moiety between the peptoid and the terminal thiol. When the peptoid is conjugated through the terminal thiol to another molecule, the diol moiety can be specifically cleaved by treatment with sodium periodate to release the two component molecules. This feature is convenient for analytical purposes to verify the nature of the conjugate.

When periodate oxidation is used to convert a dialkylsulfide to the corresponding sulfoxide, or to convert a DTT or tartaric acid derivative to an aldehyde (see (g) above), the diol system in such DTT adducts must be protected (e.g. by forming the acid labile isopropylidine derivative). The sulfur in S-acetyl-thioacetamide (intermediate shown in (b1) reaction), however, is not oxidized by periodate.

Another cleavable site useful in solid phase peptide or peptoid synthesis is a tartaric acid-based linker, as described by Fruchart et al., *Tetrahedron Lett.* 40:6225-6228 (1999).

During synthesis, the 1,2-diol moiety is protected as the isopropylidine derivative. The isopropylidine group is cleaved with standard acid treatment to give the 1,2-diol, which can then be cleaved by periodate treatment

B2. C-Terminal Modifications

Figure 7:
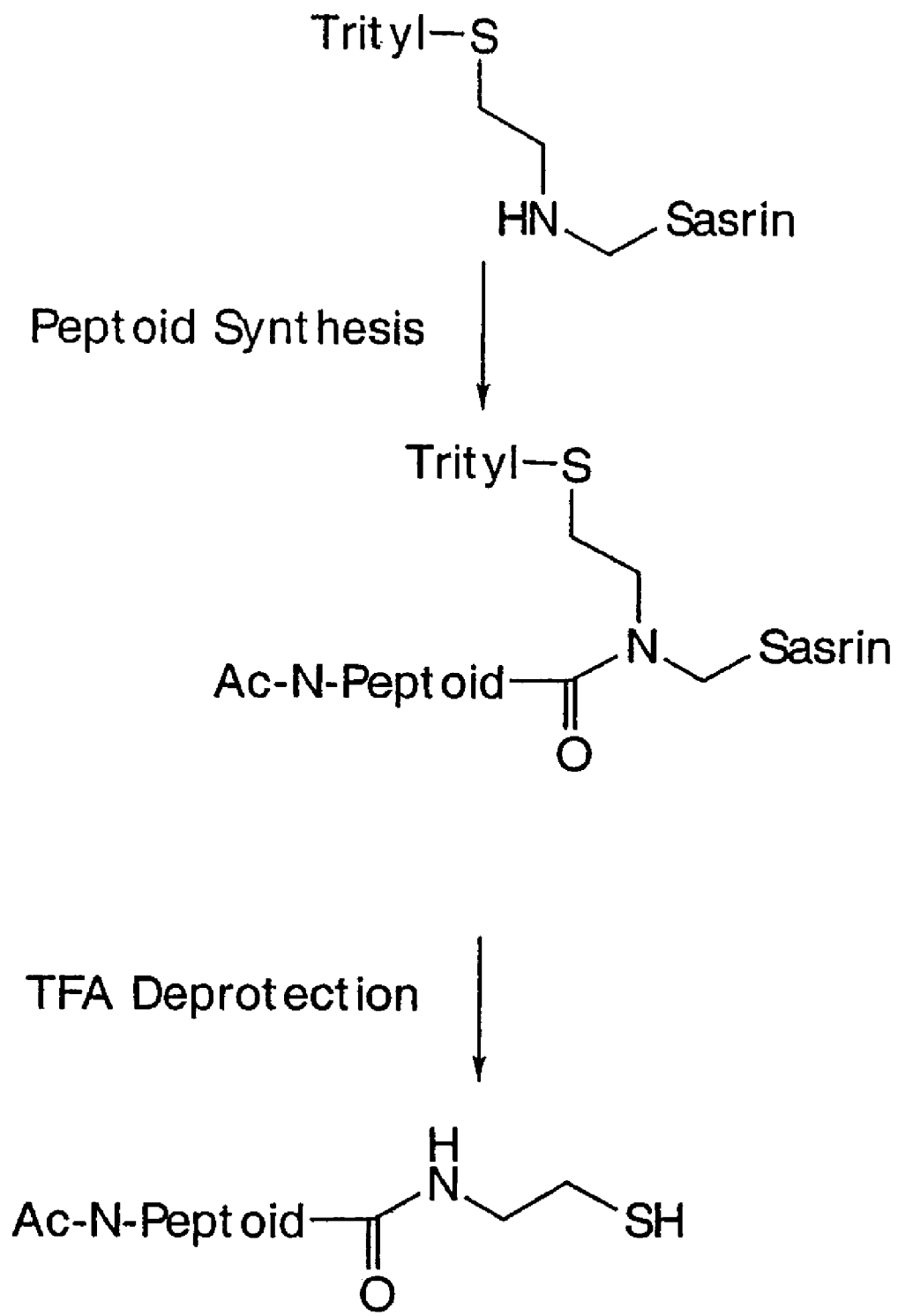
FIG. 7 illustrates C-terminal attachment of a ligation moiety to a peptoid.

In another embodiment, as stated above, an amine-derivatized solid support is employed, and a ligation moiety is attached to the amine of the solid support. Cleavage from the support provides a conjugate having a ligation moiety at the C-terminus of the molecule or spacer group; one example is shown in FIG. 7. The solid support may incorporate, for example, a protected thiol, aminooxy, hydrazino or 1,2-diol functionality. The 1,2-diol moiety can subsequently be cleaved to yield a terminal aldehyde.

Figure 9:
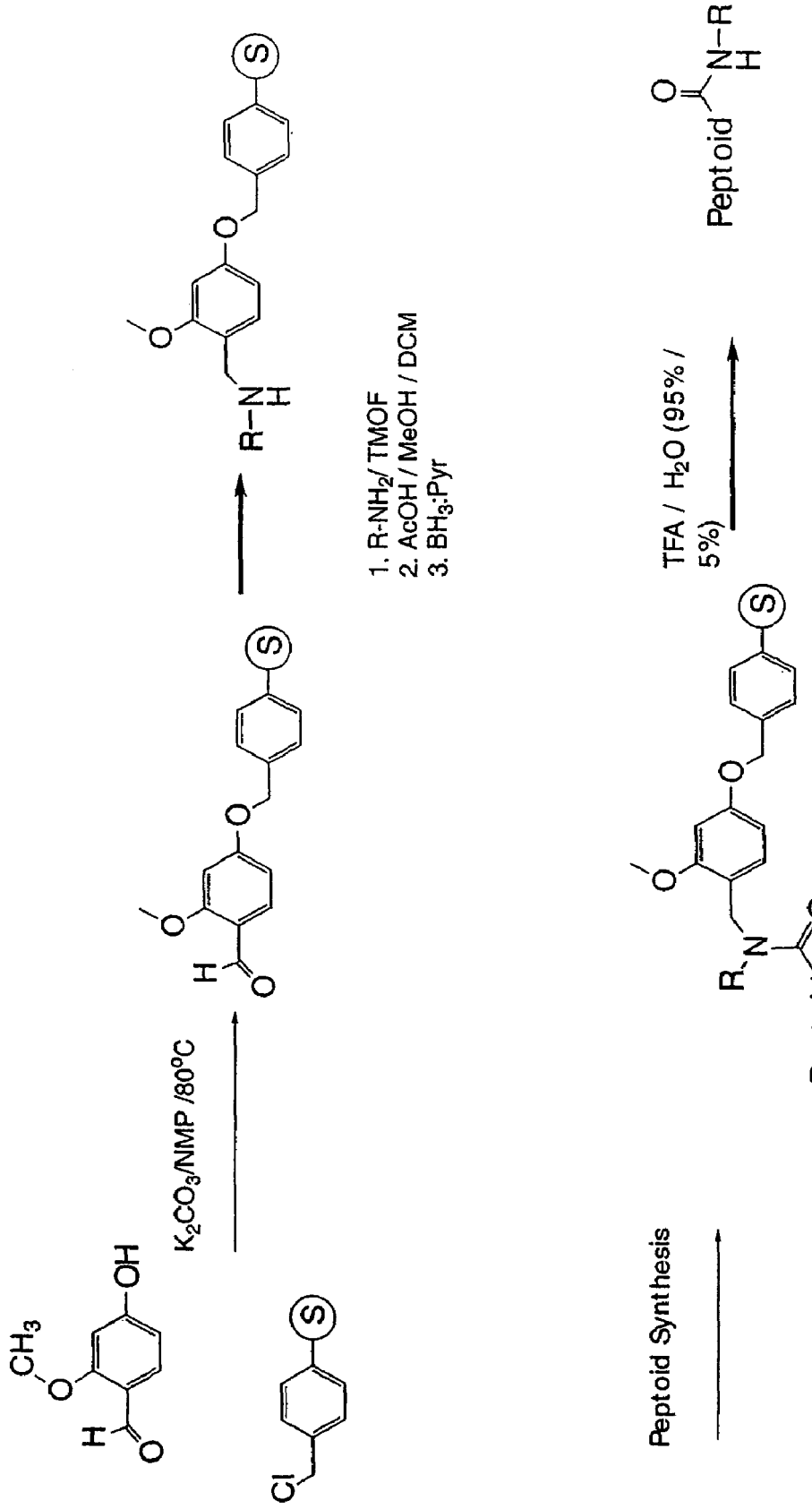
FIG. 9 shows a synthetic scheme for preparing a dedicated support which incorporates a protected ligation moiety, for preparing molecules having the ligation moiety at the C-terminus.

Such modifications can be introduced using modified Sasrin™-type supports (see e.g. Mergler et al., *Chimia* 53:29-34, 1999). As shown in FIG. 9, a chloromethylated polystyrene resin is heated with 4-hydroxy-2-methoxy-benzaldehyde to yield an aldehyde-derivatized resin. Reductive amination is used to prepare alkylamine derivatized supports. Following synthesis, peptoids are readily cleaved from the support, as the alkyl amide is labile to trifluoroacetic acid (also see FIG. 7).

Exemplary dedicated supports were prepared by reductive amination of aldehyde-derivatized resins with, respectively, N-2-(N-Boc-aminooxyacetamide)ethylenediamine, 5-aminopentano (N"-Boc-hydrazide), and S-trityl-ethylamine, and N-(11-S-trityl-undecamide) ethylenediamine, respectively.

P—NH—$CH_2CH_2$—NH—CO—$CH_2$—O—NH-Boc
P—NH—$CH_2CH_2CH_2CH_2CO$—NH—NH-Boc
P—NH—$CH_2CH_2$—S-Tr
P—NH—$CH_2CH_2$—NH—CO—$(CH_2)_{10}$—S-Tr

III. Spacer Group-Containing Conjugates

The invention also provides a hydrophilic spacer group-molecule conjugate, which may be prepared according to the above-described methods: The conjugate has the structure:

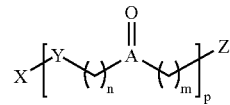

In this structure, Y is NH, O, or S; each of m and n is independently 2 to 6, preferably 2 to 4, and most preferably 2; A is S or Se; and p is 1 to 100, preferably 2 to 25. The entity [Y—(CH$_2$)$_n$-A(=O)—(CH$_2$)$_m$]$_p$ represents the spacer group, having sulfoxide or selenoxide groups represented by A=O. The spacer group is linked to entities X and Z, where one is a terminating group or a ligation moiety as described above, and the other is a molecule, such as a peptoid, a peptide or protein, an oligonucleotide, or an oligosaccharide. Terminating groups include hydrogen, alkyl, or acyl, i.e., R(C=O)— where R is alkyl, aryl, or aralkyl, preferably alkyl. The ligation moiety may be in protected form. The molecule may be joined to the spacer group via a direct bond or via a linking group. This linking group may be, for example, derived from the ligation moieties described above. Preferably, the length of the linking group, if present, is substantially less than that of the spacer group.

In one embodiment, the molecule is a peptoid. When the molecule is a peptoid or other molecule amenable to stepwise solid-phase synthesis, the conjugate can be conveniently prepared entirely in the solid phase. In additional embodiments, A represents sulfur (S), and Y is NH. In a further embodiment, n=m=2.

The invention also provides a solid phase support derivatized with at least one hydrophilic spacer group. This conjugate has the structure:

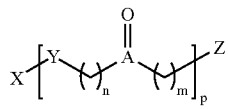

In this structure, as above, Y is NH, O, or S; each of m and n is independently 2 to 6, preferably 2 to 4, and most preferably 2; A is S or Se; and p is 1 to 100, preferably 2 to 25. The entity [Y—(CH$_2$)$_n$-A(=O)—(CH$_2$)$_m$]$_p$ represents the spacer group, having sulfoxide or selenoxide groups represented by A=O. The spacer group is linked to entities X and Z', where one is a terminating group or ligation moiety, as described above, and the other is the solid phase support. The support may be in any convenient form, such as a bead or a planar surface.

In a related embodiment, the invention provides kits containing one or more spacer-derivatized solid phase supports as described above, wherein one of group X or Z' is a ligation moiety, and the other is the solid phase support. Again, the supports may be in any convenient form, such as a bead or a planar surface. Also included in the kits are one or more populations of molecules, where each molecule contains a ligation partner moiety effective to react with the ligation moiety (X or Z') on the spacer to form a stable linkage. The molecules are preferably molecules having a biological or diagnostic activity, or which are candidates for such activity. For example, the molecules may be candidate binding agents for a biomolecule or biomolecular structure, such as an enzyme or receptor. Typical examples of molecules include peptoids, peptides or proteins, and oligonucleotides, which may be provided as combinatorial libraries of different-sequence molecules. The kits may also include other reagents such as protecting reagents, deprotecting reagents and/or solvents.

IV. Solid Phase Synthesis of Structurally Varied Peptoids

A. Branched Peptoids

Use of protected ligation moieties in submonomer peptoid syntheses, as described above, may also be used to prepare peptoids having varied structures, such as branching and disulfide crosslinks, such as shown in FIGS. 10-16. For example, a branched peptoid is prepared (see FIG. 10) as follows. A "main" peptoid chain is first synthesized on an amine-derivatized solid support by the submonomer method, i.e. by repeating alternating addition of (i) an acyl submbnomer bearing an α-leaving group and (ii) a primary amine submonomer. In this case, at least one such primary amine submonomer is a diamine, having one free primary amine and one primary or secondary amine protected with a protecting group which is not removed under the conditions of the peptoid synthesis. One such protecting group is p-nitrophenethyloxycarbonyl (NPEOC), which is removed by treatment with DBU in N-methyl pyrrolidinone.

When the synthesis of the main peptoid chain is completed, its free N-terminus is capped, e.g. by acylation. The aforementioned protecting group is then removed, to produce a free primary or secondary amine. This free amine is then used as the starting point for synthesis of the "branch" peptoid chain (which may be of any length in comparison to the "main" chain). As noted above, such branched structures can be prepared entirely in the solid phase, and because the submonomer method is used, various combinations of side chains can be incorporated.

Figure 10:
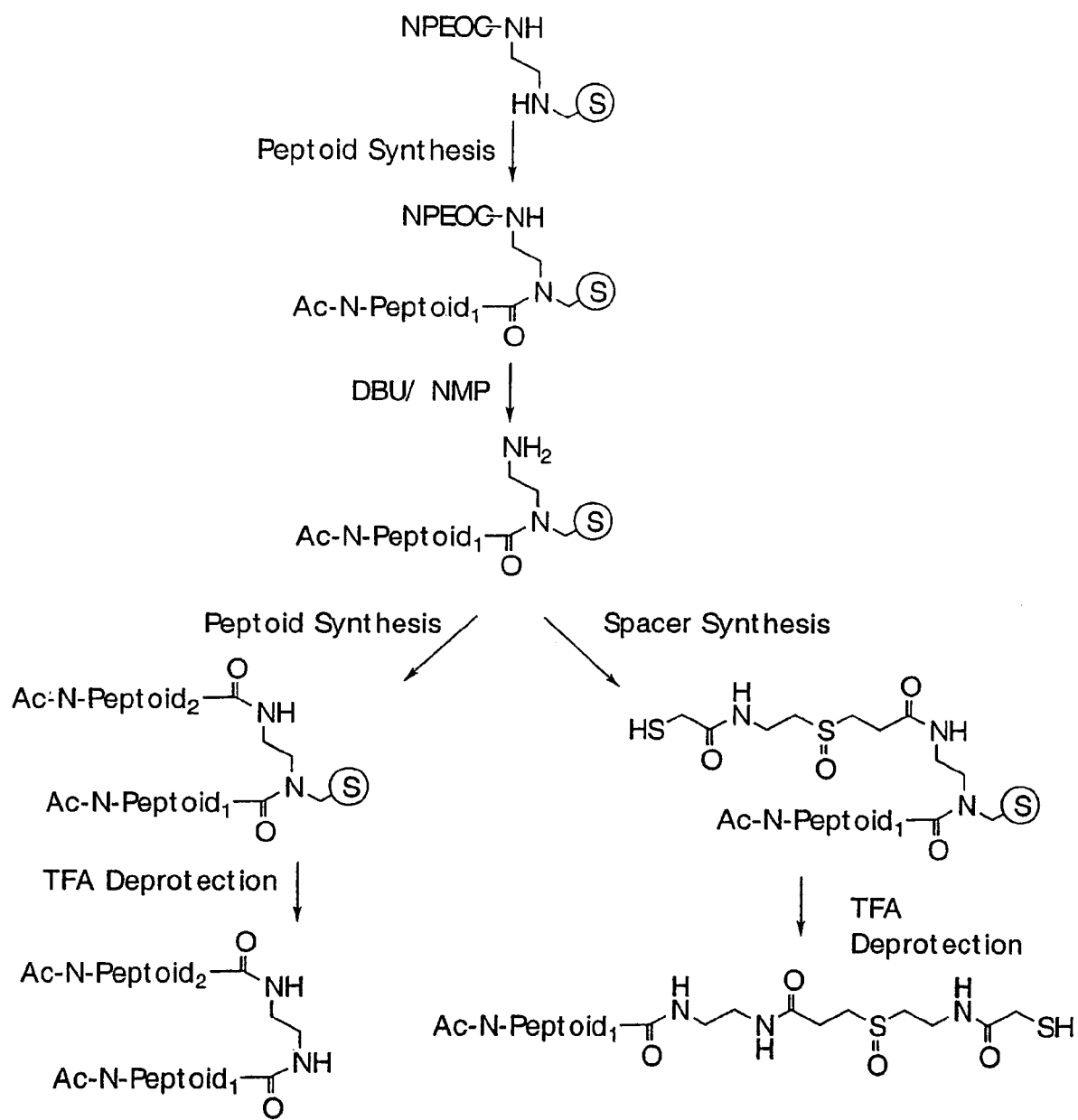
FIG. 10 shows a synthetic scheme for preparing branched peptoids.
Figure 11:
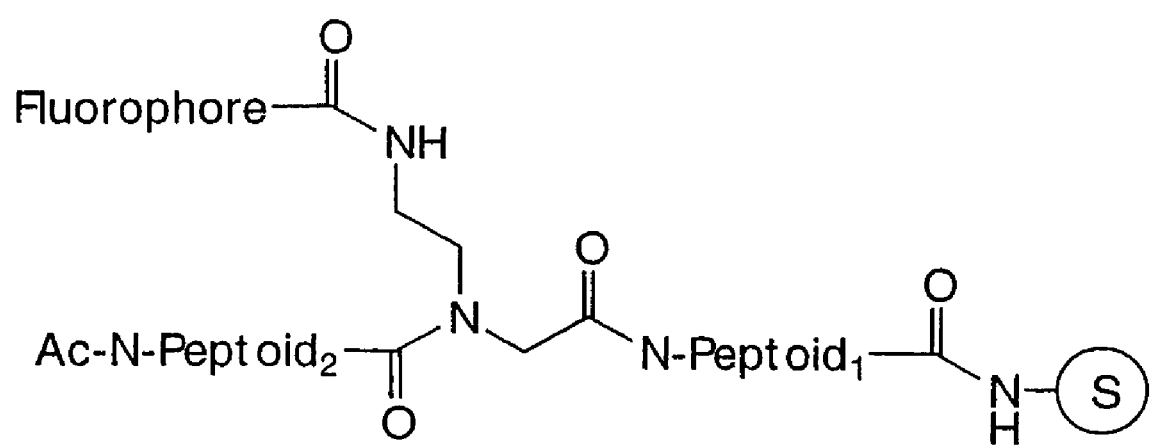
FIGS. 11-13 show several examples of branched peptoids.
Figure 12:
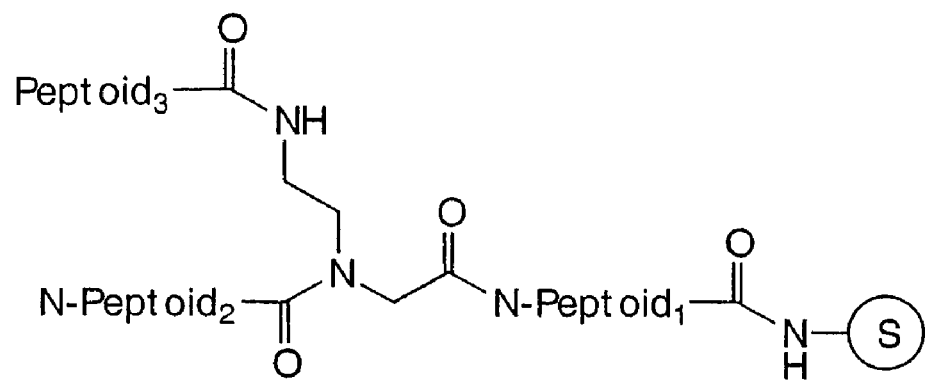
Figure 13:
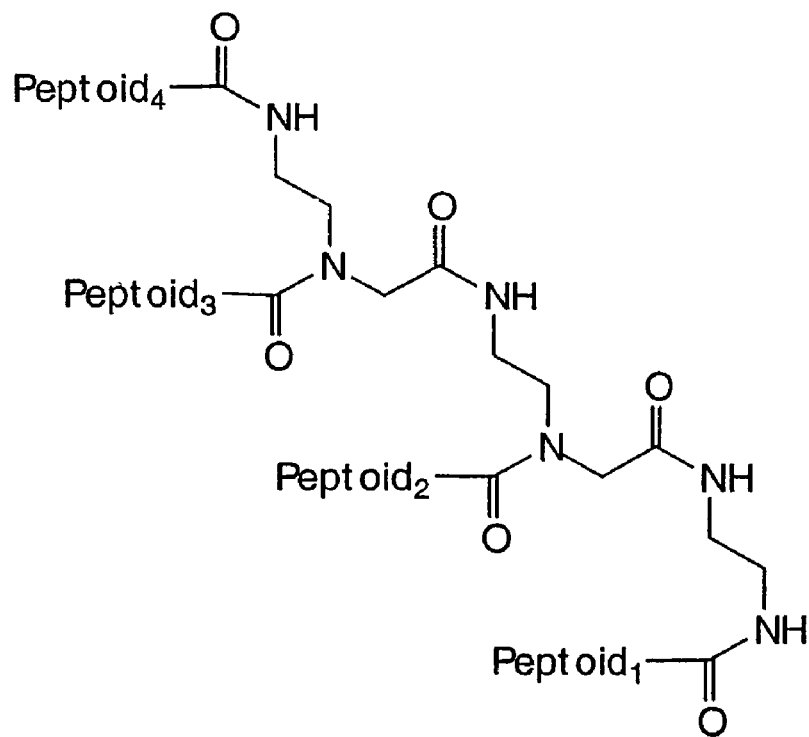

The branch chain may be terminated with a ligation moiety, to give a peptoid with an internal linker, as illustrated in FIG. 10, or it may be labeled, as shown in FIG. 11. Multiply branched peptoids, such as shown in FIGS. 12-13, can be prepared by following the synthetic sequence peptoid$_1$—cap—deprotect—peptoid$_2$—cap—deprotect, etc., where each peptoid$_n$ chain includes a monoprotected diamine as described above, and each successive peptoid$_{n+1}$ chain is appended to that diamine after deprotection.

Figure 14:
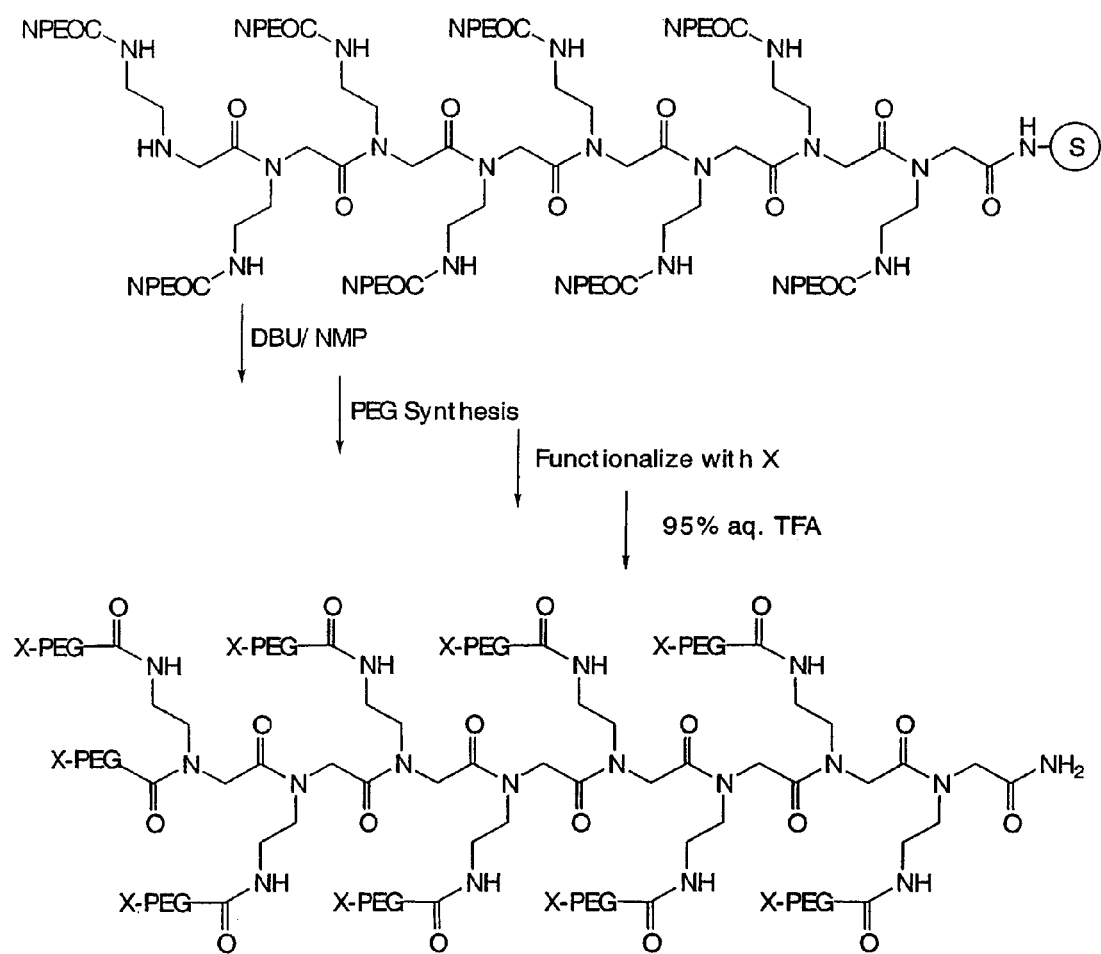
FIG. 14 shows synthesis of a "star PEG" compound from a branched peptoid "scaffold" that incorporates multiple —N—CH$_2$CH$_2$—NH-pNPEOC groups.

A "star PEG" compound (Gnanou et al., Makromol. Chem. 189, 22885-92, 1988) can be prepared from a branched peptoid "scaffold" that incorporates multiple —N—CH$_2$CH$_2$—NH— pNPEOC groups, as shown in FIG. 14. The NPEOC protecting groups are removed from all branches, and PEG chains are synthesized on each of the generated amines. A peptoid scaffold with n arms will produce a star PEG molecule with n+1 PEG chains (one from each branch+one from the N terminus). Such molecules occupy a large volume at a surface-liquid interface, are highly solvated, and provide multiple termini for further conjugation. These molecules can, for example, substitute for streptavidin assembled into protein 'monolayers' on surfaces fully derivatized with biotin (see Merrill, E. W., "Immobilized polyethylene oxide star molecules for bioapplications", U.S. Pat. No. 5,171,264). The advantage of the branched peptoid approach to synthesis, as described herein, is that the geometry of the star PEG molecules can be precisely engineered.

B. Disulfide Linked Peptoid Dimers

Because many biologically important proteins have secondary structures based on disulfide crosslinks between peptide chains, it is useful to prepare peptoids which mimic this structure. Variously protected thiol groups may be employed to prepare disulfide-linked peptoids, either as homodimers or heterodimers, from populations of support bound peptoids. In one embodiment, the populations of peptoids are combinatorial libraries of different-sequence peptoids. Because the process is carried out in the solid phase, and is amenable to preparation of libraries of different-sequence compounds, the method is especially suitable for preparing libraries of disulfide-linked peptoids. It can be seen that control of the sequence of events (deprotection, cleavage from supports, mixing of beads) can be used to prepare either homodimers or heterodimers, as described below.

Figure 15:
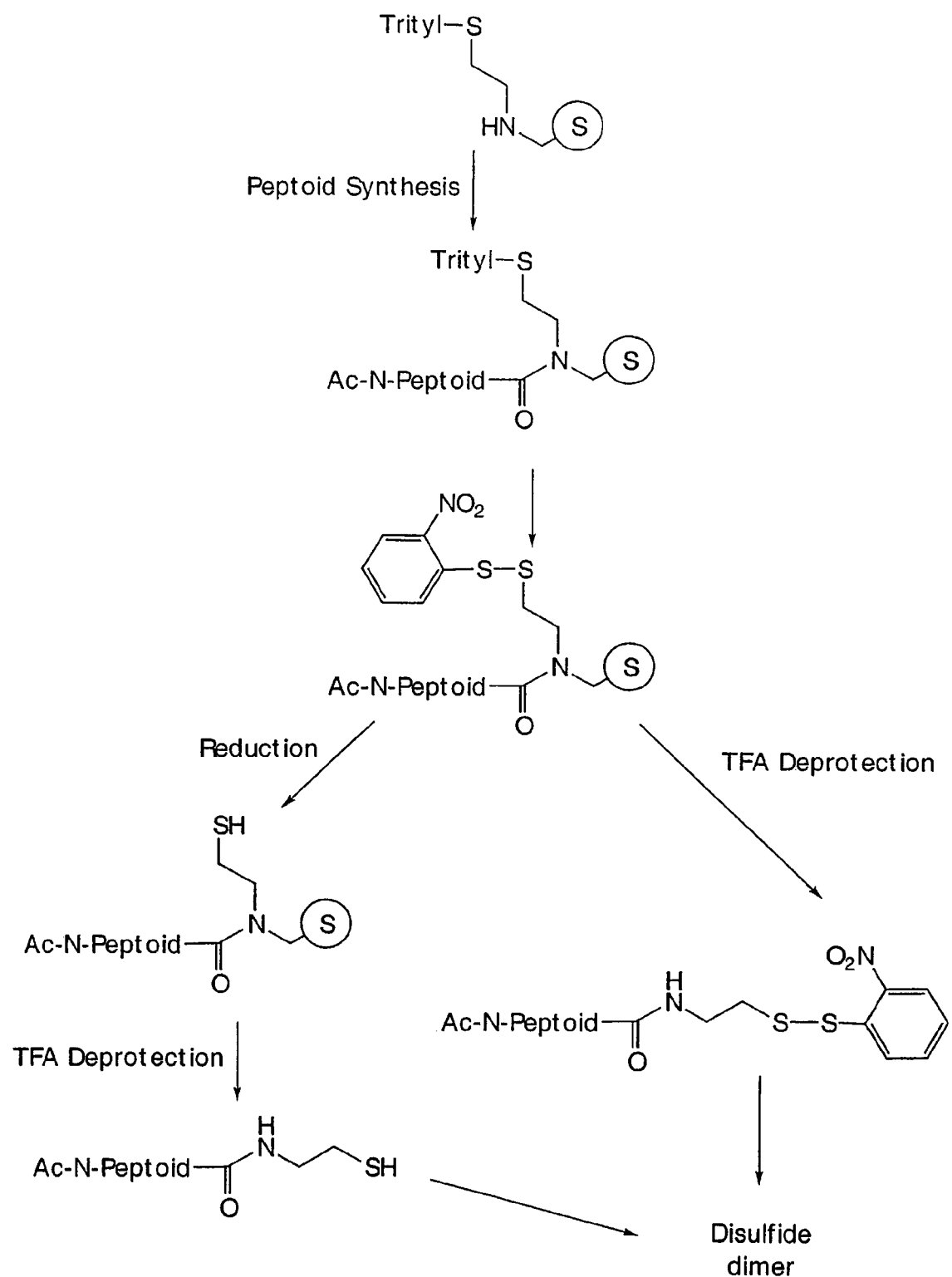
FIGS. 15 and 16 show synthetic schemes for the solid phase synthesis of diverse sets of disulfide-linked peptoid dimers.

One embodiment of the method, which can be used to prepare heterodimers, is carried out as follows (FIG. 15). A first population of solid support bound-peptoids is provided, where each peptoid is derivatized with a thiol or S-trityl group. The first population of peptoids may be prepared by submonomer synthesis, as described above, where a thiol- or S-trityl-terminated ligation moiety is attached at a terminus. In the scheme shown in FIG. 15, the ligation moiety is attached to the nitrogen atom of the solid support upon which the peptoid is built (see C-terminal modifications, above). The ligation moiety could also be attached at the N-terminus or at an internal branch, also using methods described above.

A second population is provided where each peptoid is derivatized with an activated disulfide, such as the reaction product of a thiol with o-nitrosulfenyl chloride. The second population is prepared, similarly, by submonomer synthesis and attachment of a ligation moiety. The activated disulfide can be provided by attaching a thiol- or S-trityl-terminated ligation moiety, as for the first population, and then reacting the construct with o-nitrosulfenyl chloride, or by directly attaching a ligation moiety terminated with the activated disulfide.

In one embodiment of this method, a library of solid-support bound peptoids, each derivatized with a thiol or protected thiol group, such as tert-butyl sulfide (S-tert-butyl) or trityl sulfide (S-trityl), is reacted with o-nitrosulfenyl chloride to produce an activated disulfide. To produce the first population described above, a portion of this library is exposed to reducing conditions, to convert the activated disulfide to a free thiol. The balance is retained as the second population.

To prepare the library of disulfide-linked peptoid dimers, the first and second populations above are contacted, and the peptoids are cleaved from the solid supports, such that the free thiol and activated disulfide groups are able to react to form disulfide crosslinks. Contacting the populations can comprise, for example, placing one bead from each population in a microtiter well.

In an alternate method, which can be used to prepare homodimers, each peptoid in a population of solid support bound-peptoids is derivatized with a trityl sulfide (S-trityl) group. Again, the population is preferably a library of different-sequence peptoids prepared by the submonomer method. The solid support bound-peptoids are then treated with a reagent effective to cleave the thiol protecting group, allowing the formation of disulfide-linked peptoid dimers. In library synthesis methods which provide a single sequence of peptoid per bead, these alternate methods are expected to produce primarily or exclusively homodimers, as the peptoids will crosslink with peptoids on the same bead.

Figure 16:
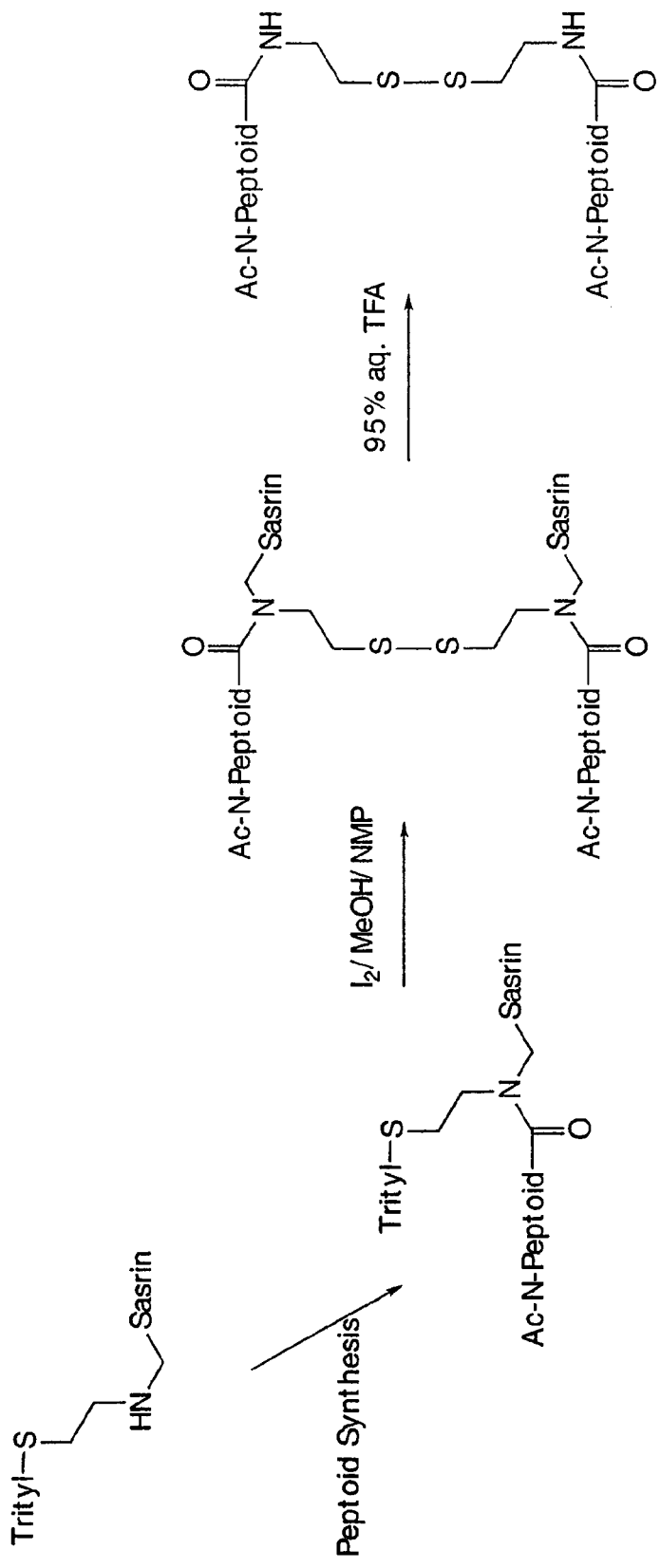

In one embodiment, as shown in FIG. 16, the reagent is iodine, which cleaves the thiol protecting group, but leaves the dimerized peptoids bound to the support. In another embodiment, the reagent is TFA/MeSiCl$_3$, which both cleaves the thiol protecting group and cleaves the dimerized peptoids from the solid support.

EXAMPLES

The following examples illustrate but are not intended in any way to limit the invention.

Example 1

Loading Sasrin™ Linker on "BigBeads" (BB)

In a dry 5 L 3-neck flask under argon, 112 g K$_2$CO$_3$ and 123 g 4-hydroxy-2-methoxy benzaldehyde were dissolved in 3.5 L anhydrous NMP by shaking the flask at 100 rpm using a gyrotary shaker equipped with suitable bars to secure the flask. "BigBeads" (Polymer Laboratories PL-CMS chloromethyl Merrifield resin, 400-500µ in diameter; 1.0 meq/g; 450 g) was added and the mixture was degassed and shaken for 15 minutes. The solution was heated to 120° C. under argon and shaken for 14 hours at 100 rpm (external heating mantle @ 125° C.). The resin was washed and dried using the following wash sequence: 1×DMF, 2×H$_2$O, 2×DMF, 2×H$_2$O, 2×DMF, 1×H$_2$O, 1× DMF (shake overnight), 1× dichloromethane, 1×glacial acetic acid, 1× water, 8×DMF, 1× methanol, 2× dichloromethane, and finally 2× diethyl ether. Wash volumes were typically 2-3 L (see solvents below) for 450 g resin, and minimum wash time was 15 minutes with shaking at room temperature. Wash solvent was removed using a large dispersion tube under vacuum with a suitable trap. After the final ether wash the resin was placed under house vacuum for 1 day and high vacuum for 1 day.

Example 2

Reductive Amination of Sasrin™ Aldehyde Linker on "BigBeads"

To 5 g of aldehyde resin, prepared as described in Example 1, in a Falcon 50 mL test tube was added 5 mL benzylamine in 40 mL trimethylorthoformate (TMOF), and the tube was shaken for 18 hours. The liquid was removed by inverse filtration using a gas dispersion tube under vacuum. The resin was quickly washed three times with anhydrous dichloromethane. Fifty mL of a mixture of CH$_2$Cl$_2$/methanol/glacial acetic acid (2:2:1 v/v) was added, followed by 1.1 mL of borane-pyridine complex. The Falcon test tube was capped and shaken for 18 hours to effect complete reduction. The resin was washed with 1×DMF, 1×H$_2$O, 3×DMF, 3× dichloromethane, 2× methanol, and finally 2× diethyl ether. After the final ether wash, the resin was placed under house vacuum for 1 day and high vacuum for 1 day, to give the final benzylamine Sasrin™ "BigBead" support.

Other Sasrin™ based supports were prepared in a similar manner.

Example 3

Poly(propylene Sulfoxide) Spacer Synthesis

A suitable solid support (100 µmoles) was provided in a small reaction vessel. Suitable derivatized solid supports include, for example, Rink-BB or Tr-S—CH$_2$CH$_2$—NH-Sasrin™-BB (amine terminated) or solid supported peptoid, e.g. H-Peptoid-N(CH$_2$CH$_2$—S-Tr)Sasrin™-BB.

Step 1: A 1M solution of acrylic acid in NMP containing 2 mmole DIC (2 mL) was added, and the mixture was incubated for 1 hour, drained and washed with NMP.

Step 2: A 1M solution of HS—CH$_2$CH$_2$CH$_2$—OH in NMP containing 200 µL DBU (2 mL) was added, and the mixture was incubated for 1 hour, drained and washed with NMP.

Step 3: A 1M solution of methanesulfonic anhydride in NMP containing 200 µL N-methylimidazole (2 mL) was added, and the mixture was incubated for 1 hour, drained and washed with NMP.

Steps 2 and 3 were repeated n times to construct the spacer.

Step 4: A 1M solution of HS—CH$_2$CH$_2$CH$_2$—OH in NMP containing 200 µL DBU (2 mL) was added, and the mixture was incubated for 1 hour, drained and washed with NMP to terminate the spacer in an amine functionality.

If appropriate, solid phase synthesis of peptoid (or other molecule) was continued. To oxidize the sulfide linkages of the spacer to the corresponding sulfoxides, 2 mL of a 1M solution of tetrabutylammonium periodate in 95% aqueous NMP were added, and the mixture was incubated for 1 hour, then drained and washed with NMP.

Example 4

Sulfoxide-Amide Spacer Synthesis

A suitable solid support (100 µmoles) was provided in a small reaction vessel. Suitable derivatized solid supports include, for example, Rink-BB or Tr-S—$CH_2CH_2$—NH-Sasrin™-BB (amine terminated) or solid supported peptoid, e.g. H-Peptoid-N($CH_2CH_2$—S-Tr)-Sasrin™-BB.

Step 1: A 1M solution of acrylic acid in NMP containing 2 mmole DIC (2 mL) was added, and the mixture was incubated for 1 hour, drained and washed with NMP.

Step 2: A 1M solution of HS—$CH_2CH_2$—$NH_2$ (as the free amine) in NMP containing 200 µL DBU (2 mL) was added, and the mixture was incubated for 1 hour, drained and washed with NMP.

Steps 1 and 2 were repeated n times to construct the spacer.

If appropriate, solid phase synthesis of peptoid (or other molecule) was continued. To oxidize the sulfide linkages of the spacer to the corresponding sulfoxides, 2 mL of a 1M solution of $NBu_4IO_4$ in 95% aqueous NMP were added, and the mixture was incubated for 1 hour, then drained and washed with NMP.

Example 5

PEG-Containing Spacer Synthesis

A suitable solid support (100 µmoles) was provided in a small reaction vessel. Suitable derivatized solid supports include, for example, Rink-BB or Tr-S—$CH_2CH_2$—NH-Sasrin™-BB (amine terminated) or solid supported peptoid, e.g. H-Peptoid-N($CH_2CH_2$—S-Tr)Sasrin™-BB.

Step 1: A 1M solution of diglycolic anhydride in NMP containing 2 mmol N-methyl imidazole was added, and the mixture was incubated for 1 hour, drained and washed with NMP.

Step 2: A 2.2M solution of 4,7,10-Trioxa-1,13-tridecanediamine in NMP containing 0.5 M N-hydroxybenztriazole was added, and the mixture was incubated for 1 hour, drained and washed with NMP.

Steps 1 and 2 were repeated n times to construct the spacer. If appropriate, solid phase synthesis of peptoid (or other molecule) was continued.

To introduce a cleavable site in the spacer, O,O-isopropylidine tartaric anhydride can be substituted for diglycolic anhydride in Step 1.

Example 6

Synthesis of Peptoid Spacer with Sulfoxide Side Groups

A suitable solid support (100 µmoles) was provided in a small reaction vessel. Suitable derivatized solid supports include, for example, Rink-BB or Tr-S—$CH_2CH_2$—NH-Sasrin™-BB (amine terminated) or solid supported peptoid, e.g. H-Peptoid-N($CH_2CH_2$—S-Tr)Sasrin™-BB.

During a peptoid synthesis using the standard submonomer protocol, the monomer Tr-S—$CH_2CH_2$—$NH_2$ was incorporated in the first (or last) n cycles, followed by (or following, respectively) synthesis of a peptide (or other oligomeric molecule) of the desired sequence. The resulting compound was left attached to the solid support.

Step 1: A 1M solution of 2-nitrobenzenesulfenyl chloride in dichloromethane containing 0.5 mL glacial acetic acid (2 mL) was added, and the mixture was incubated for 1 hour, drained and washed extensively with dichloromethane.

Step 2: A 1M solution of tributylphosphine in 95% aqueous NMP (2 mL) was added, and the mixture was incubated for 1 hour, drained and washed with NMP.

Step 3: A 1M solution of methyl 4-toluenesulfonate in NMP containing 200 µL DBU (2 mL) was added, and the mixture was incubated for 1 hour, drained and washed with NMP.

To oxidize the sulfide linkages of the spacer to the corresponding sulfoxides, 2 mL of a 1M solution of tetrabutylammonium periodate in 95% aqueous NMP were added, and the mixture was incubated for 1 hour, then drained and washed with NMP.

Example 7

Synthesis of Dedicated Spacer Molecule, FMOC-NH-'PEG'-COOH

To a 2 L round bottom flask containing 200 mmole 4,7,10-trioxa-1,13-tridecanediamine in 1000 mL DCM, cooled to −20° C., was slowly added FMOC-Cl (50 mmoles) in DCM over 60 minutes. Next was added solid diglycolic anhydride (400 mmoles) followed by 1 mL N-methylimidazole, 50 mmoles 2,4,6-collidine, and 250 mL methanol, and the solution was allowed to warm to room temperature. The solvents were removed at reduced pressure to yield an oil, which was suspended in 1 L water (and the pH adjusted to ca. 2 if needed with 6M aq. HCl). The product was isolated by extraction with 1 L ethyl acetate, the organic phase dried over $Na_2SO_4$, and the solvent removed at reduced pressure to give 25.5 grams of a slightly yellow oil (45.7 mmoles; 90% product plus 10% $FMOC_2$-4,7,10-trioxa-1,13-tridecanediamine). TLC (10% methanol/dichloromethane 1:1 v/v, containing 2% acetic acid) Rf=0.25.

The product was used without further purification, as a solution in NMP (total volume 100 mL) containing 0.5 M HOBt, for spacer synthesis on an automated synthesis apparatus.

Example 8

Incorporation of N-terminal Spacer

A suitable solid support (100 µmoles) was provided in a small reaction vessel. Suitable derivatized solid supports include, for example, Rink-BB or Tr-S—$CH_2CH_2$—NH-Sasrin™-BB (amine terminated) or solid supported peptoid, e.g. H-Peptoid-N($CH_2CH_2$—S-Tr)Sasrin™-BB.

Step 1: A 0.5M solution of FMOC-NH-PEG-COOH in NMP containing 0.5 M N-hydroxybenztriazole (2 mL) was added, followed by 1 mmole DIC, and the mixture was incubated for 1 hour, drained and washed with NMP.

Step 2: A 20% solution of piperidine/DMF (2 mL) was added, and the mixture was incubated for 1 hour, drained and washed with NMP.

Steps 1 and 2 can be repeated to extend the spacer to the desired length.

Step 3: To produce the terminal thiol functionality, a 0.5M solution of Tr-S—$CH_2CH_2$—COOH in NMP containing 0.5

M N-hydroxybenztriazole (2 mL) was added, followed by 1 mmole DIC, and the mixture was incubated for 1 hour, drained and washed with NMP.

In Step 3, any other suitably protected carboxylic acid may be substituted for Tr—S—CH$_2$CH$_2$—COOH to terminate the spacer in another desired functionality; examples are Boc-HN—O—CH$_2$—COOH and Boc-HN—NH—CO—CH$_2$CH$_2$—COOH.

Example 9

Synthesis of C-Terminal Spacer (or Peptoid) onto Solid Supported Peptoid

A solid support (NPEOC—NH—CH$_2$CH$_2$—NH-Sasrin™-BB, 100 µmoles) was provided in a small reaction vessel, and peptoid synthesis was carried out using the standard submonomer protocol. To cap the N terminus as the N-acetamide, 2 mL of a 0.5 M solution of acetic anhydride in pyridine were added, and the mixture was incubated for 1 hour, then drained and washed with NMP.

To specifically remove the NPEOC protection group from the solid supported peptoid, 2 mL of a 0.5 M solution of DBU in NMP were added, and the mixture was incubated for 1 hour, then drained and washed with NMP. Peptoid or spacer synthesis was carried out on the generated amine group, terminating in a suitable functionality.

While the invention has been described with reference to specific methods and embodiments, it will be appreciated that various modifications may be made without departing from the invention.

What is claimed is:

1. A hydrophilic spacer group-molecule conjugate having the structure:

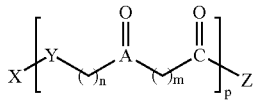

where
Y is NH, O, or S,
each of m and n is independently 2 to 6;
A is S or Se,
p is 1 to 100,
one of X and Z is a terminating group or ligation moiety, and the other is a molecule selected from a peptide, a peptide, an oligonucleotide, and an oligosaccharide, joined to said spacer group via an optional linking group.

2. The conjugate of claim 1, wherein said molecule is a peptoid.

3. The conjugate of claim 1, wherein A is S.
4. The conjugate of claim 3, wherein n=m=2.
5. The conjugate of claim 4, wherein p is 2 to 25.
6. The conjugate of claim 5, wherein Y is NH.
7. The conjugate of claim 1, wherein the ligation moiety comprises a functional group selected from the group consisting of: thiol, disulfide, hydroxyl, amino, carboxylic acid, thioester, thiocarboxylic acid, aldehyde, hydrazine, hydrazide, 3-mercapto-1,2-propanediyl, aminooxyacetyl, N-(2-thioethyl)amino, N-(2-hydroxyethyl)amino, 2-bromo amino acid, biotin, and protected derivatives thereof.

8. The conjugate of claim 2, wherein the peptoid has the general formula I:

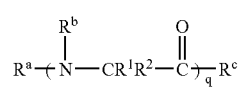

where
$R^a$ is selected from the group consisting of alkyl, aryl, aralkyl, aralkenyl, and aralkynyl, any of which may be substituted with one or more groups W, hydrogen, —OH, —SH, —COOH, sulfonyl, and a lipid moiety, wherein the lipid moiety may be conjugated to a linker moiety,
each $R^b$ is independently selected from the group consisting of alkyl, aryl, aralkyl, aralkenyl, and aralkynyl, any of which may be substituted with one or more groups W, and hydrogen, where at least one group $R^b$ is not hydrogen;
$R^c$ is selected from the group consisting of alkyl, aryl, aralkyl, aralkenyl, and aralkynyl, any of which may be substituted one or more groups W; hydrogen, —OH, —SH, —NH$_2$, —NHR, —NH(C=O)R, where R is lower alkyl; sulfonyl, hydrazine, and a lipid moiety, wherein the lipid moiety may be conjugated to a linker moiety;
$R^1$ and $R^2$ are independently selected from hydrogen, lower alkyl, and lower alkoxy;
W is selected from hydroxy, alkoxy, amino, guanidino, amidino, alkylamino, alkylthio, halogen, nitro, cyano, keto, aldehyde, carboxylic acid, carboxylic ester, carboxylic amide, sulfonic acid and sulfonic ester; and
q is an integer selected from 2 to about 50.

9. The conjugate of claim 8, wherein, in said peptoid, each of $R^1$ and $R^2$ is hydrogen.

10. The conjugate of claim 9, wherein, in said peptoid, at least one $R^b$ includes a group which is cationic at physiologically relevant pH, and at least one $R^b$ is uncharged at physiologically relevant pH.

* * * * *